United States Patent
Lee et al.

(10) Patent No.: US 11,266,650 B2
(45) Date of Patent: Mar. 8, 2022

(54) PHARMACEUTICAL COMPOSITION FOR PREVENTING AND TREATING NONALCOHOLIC STEATOHEPATITIS, HEPATIC FIBROSIS, AND LIVER CIRRHOSIS, COMPRISING ADENOSINE DERIVATIVES

(71) Applicant: FUTURE MEDICINE CO., LTD., Seongnam-si (KR)

(72) Inventors: Sang Koo Lee, Seoul (KR); Chong Woo Park, Seoul (KR)

(73) Assignee: FUTURE MEDICINE CO., LTD., Seongnam-si (KR)

( * ) Notice: Subject to any disclaimer, the term of this patent is extended or adjusted under 35 U.S.C. 154(b) by 126 days.

(21) Appl. No.: 16/345,724

(22) PCT Filed: Oct. 23, 2017

(86) PCT No.: PCT/KR2017/011744
§ 371 (c)(1),
(2) Date: Apr. 29, 2019

(87) PCT Pub. No.: WO2018/080127
PCT Pub. Date: May 3, 2018

(65) Prior Publication Data
US 2020/0046711 A1    Feb. 13, 2020

(30) Foreign Application Priority Data
Oct. 31, 2016    (KR) .................. 10-2016-0142723

(51) Int. Cl.
*A61K 31/52* (2006.01)
*A61P 1/16* (2006.01)
*A61K 9/00* (2006.01)
*A61K 47/38* (2006.01)

(52) U.S. Cl.
CPC .......... *A61K 31/52* (2013.01); *A61K 9/0053* (2013.01); *A61K 47/38* (2013.01); *A61P 1/16* (2018.01)

(58) Field of Classification Search
CPC .................... A61K 31/52; A61P 1/16
See application file for complete search history.

(56) References Cited

U.S. PATENT DOCUMENTS

| | | |
|---|---|---|
| 2007/0219221 A1 | 9/2007 | Zeng et al. |
| 2008/0188495 A1 | 8/2008 | Kobayashi et al. |
| 2010/0137577 A1 | 6/2010 | Jeong et al. |
| 2012/0252823 A1 | 10/2012 | Jacobson et al. |
| 2013/0165399 A1 | 6/2013 | Kohno et al. |

FOREIGN PATENT DOCUMENTS

| | | |
|---|---|---|
| CN | 101801970 A | 8/2010 |
| JP | 2010-520271 A | 6/2010 |
| JP | 2012-211191 A | 11/2012 |
| KR | 10-1428113 B1 | 8/2014 |
| KR | 10-1709307 B1 | 2/2017 |

OTHER PUBLICATIONS

International Search Report for PCT/KR2017/011744 dated Jan. 25, 2018 from Korean Intellectual Property Office.
Jacobson, K. A. et al., "Adenosine Receptors: Pharmacology, Structure-Activity Relationships, and Therapeutic Potential", J. Med. Chem., 35, 407-422, 1992.
Zhou, Q. Y, et al., "Molecular cloning and characterization of an adenosine receptor: The A3 adenosine receptor", Proc. Natl. Acad. Sci., U.S.A., 89, 7432-7436, 1992.
Ramkumar, V. et al., "The A3 Adenosine Receptor is the Unique Adenosine Receptor Which Facilitates Release of Allergic Mediators in Mast Cells", J. Biol. Chem., 268, 168871-168890, 1993.
Abbracchio, M. P. et al., "G protein-dependent activation of phospholipase C by adenosine A3 receptors in rat brain", Mol. Pharmacol., 48, 1038-1045, 1995.
Baraldi, P. G. et al., "Pyrazolo[4,3-e]1,2,4-Triazolo[1,5-c]Pyrimidine Ligands, New Tools to Characterize A3 Adenosine Receptors in Human Tumor Cell Lines", Curr. Med. Chem., 12, 1319-1329, 2005.
Kim, S-K. et al., "Docking studies of agonists and antagonists suggest an activation pathway of the A3 adenosine receptor", J. Mol. Graph. Model., 25, 562-577, 2006.
S. Bar-Yehuda et al., "The A3 adenosine receptor agonist CF102 induces apoptosis of hepatocellular carcinoma via de-regulation of the Wnt and NF-κB signal transduction pathways", International Journal of Oncology 33: 287-295, 2008.
Pnina Fishman et al., "The A3 adenosine receptor agonist, namodenoson, ameliorates non-alcoholic steatohepatitis in mice", International Journal of Molecular Medicine, Dec. 2019; 44(6): 2256-2264.

(Continued)

*Primary Examiner* — Savitha M Rao
*Assistant Examiner* — Gregg Polansky
(74) *Attorney, Agent, or Firm* — Revolution IP, PLLC

(57) ABSTRACT

A pharmaceutical composition for preventing or treating liver disease is provided. The pharmaceutical composition comprising a compound represented by formula 1 below or a pharmaceutically acceptable salt of the compound as an active ingredient:

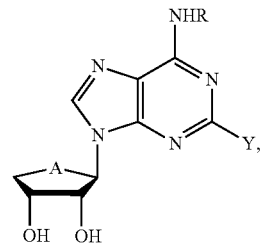

where A is S, R is a linear or branched $C_1$-$C_5$ alkyl which is non-substituted or is independently or selectively substituted with one or more $C_6$-$C_{10}$ aryl groups, a benzyl which is non-substituted or is independently or selectively substituted with halogen or one or more linear or branched $C_1$-$C_4$ alkoxy groups, or a hydroxycarbonyl-substituted benzyl, and Y is H or a halogen atom.

2 Claims, 18 Drawing Sheets

(56) References Cited

OTHER PUBLICATIONS

Jiyoun Lee et al., "The Selective A3AR Antagonist LJ-1888 Ameliorates UUO-Induced Tubulointerstitial Fibrosis", The American Journal of Pathology, vol. 183, No. 5, Nov. 2013.

PHARMACEUTICAL COMPOSITION FOR PREVENTING AND TREATING NONALCOHOLIC STEATOHEPATITIS, HEPATIC FIBROSIS, AND LIVER CIRRHOSIS, COMPRISING ADENOSINE DERIVATIVES

CROSS REFERENCE TO PRIOR APPLICATIONS

This application is the 35 U.S.C. 371 national stage of International application PCT/KR2017/011744 filed on Oct. 23, 2017; which claims priority to Korean application 10-2016-0142723 filed on Oct. 31, 2016. The entire contents of each of the above-identified applications are hereby incorporated by reference.

TECHNICAL FIELD

The present invention relates to a pharmaceutical composition having adenosine derivative for preventing or treating liver disease and, by extension, for preventing or treating nonalcoholic steatohepatitis (NASH) or nonalcoholic fatty liver disease (NAFLD), liver fibrosis and liver cirrhosis.

BACKGROUND ART

Adenosine is a ligand which regulates cell signaling, which accounts for various physiological functions through specific adenosine receptors located in the cell membrane. Adenosine, an extracellular substance, acts as a neurotransmitter in a variety of physical systems, typically functioning to compensate for overactivity of certain organs and protect the body from the harmful effects of stress (Jacobson, K. A. et al., J. Med. Chem., 35, 407-422, 1992). These functions are based on a part of the negative feedback loop in which adenosine, formed through the dephosphorylation of endocellular or extracellular ATP (adenosine triphosphate), decreases the cellular energy and increases oxygen supply. Adenosine plays an important role in maintaining the homeostasis of organs such as the brain, the heart and the kidneys. For example, an adenosine agonist was proven to show neuroprotective effects when externally administered to the brain, and was also found to be involved in pain, recognition, exercise and sleep.

Pharmacological research and molecular cloning studies have revealed two classes (P1 and P2) of adenosine receptors. Adenosine acts as a substrate for P1 receptor, while ATP, ADP, UTP and UDP act as substrates for P2 receptor. In P1 receptor, four different subtypes of adenosine receptors have been found. They can be divided into $A_1$, $A_2$ and $A_3$ according to ligand affinity, distribution within the body, and functional pathway, and $A_2$ is further divided into $A_{2A}$ and $A_{2B}$. These adenosine receptors are members of the G-protein-coupled receptor family. Pharmacological functions of adenosine $A_1$, $A_{2A}$ and $A_{2B}$ receptors have been revealed using various selective ligands. As for the $A_3$ receptor, it was first identified in 1992 (Zhou, Q. Y, et al., Proc. Natl. Acad. Sci., U.S.A., 89, 7432-7436, 1992) and its pathophysiological functions have been extensively studied.

Adenosine $A_1$ and $A_2$ receptor agonists, as adenosine derivatives, have been intensively studied for use as hypotensive agents, therapeutics for mental illness and arrhythmia, lipid metabolism suppressant (therapeutics for diabetes) and neuroprotectives. On the other hand, their antagonists, xanthine derivatives or in the form of two or more fused heterocyclic compounds, are developed as anti-asthmatics, anti-depressants, anti-arrhythmics, renal protectants, drugs for Parkinson's disease, and intelligence enhancers. Despite extensive study, only a few commercial products have been developed, including adenosine itself for the treatment of supraventricular tachycardia, and dipyridamole, the adenosine transfer inhibiting drug, which is used as a supplemental drug for warfarin in preventing blood coagulation after cardiotomy. The reason for little progress toward the commercialization of adenosine derivatives is that adenosine receptors are distributed throughout the body, and the activation thereof is accompanied by various pharmaceutical activities. In brief, there are no compounds that are able to activate only the adenosine receptors of a desired tissue.

The function of the adenosine $A_3$ receptor, the most recently identified, remains unknown, in contrast to the $A_1$ and $A_2$ receptors, the functions of which are well known. Extensive research has been conducted to develop a selective receptor regulator. In this regard, three radiolabeled ligands [$^{125}$I]ABA ($N^6$-(4-amino-3-[$^{125}$I]iodobenzyl)-adenosine), [$^{125}$I]APNEA ($N^6$-2-(4-amino-3-[$^{125}$I]iodophenyl)-ethyl adenosine) and [$^{125}$I]AB-MECA ($N^6$-(4-amino-3-[$^{125}$I]iodobenzyl)-adenosine-5'-N-methylcarboxamide) are currently used for the pharmacological study of adenosine $A_3$ receptor. For example, it was found through research on the radiolabeled ligands that when expressed in Chinese Hamster Ovary (CHO) cells, the $A_3$ receptor inhibited adenylyl cyclase, an enzyme that produces cAMP from ATP. Also, when activated by agonists, the $A_3$ receptor was proven to mediate the activation of guanosine triphosphate-dependent phospholipase C, an enzyme which catalyzes the degradation of phosphatidyl inositol into inositol triphosphate and diacylglycerol (DAG) in the brain (Ramkumar, V. et al., J. Biol. Chem., 268, 168871-168890, 1993; Abbracchio, M. P. et al., Mol. Pharmacol., 48, 1038-1045, 1995). These findings indicate the possibility that there is a reaction pathway mediated by the $A_3$ receptor in cerebral ischemia when it is activated. The reason is that this second messenger system acts as a reaction pathway leading to nerve injury in cerebral ischemia. Also, $A_3$ receptor agonists are known to prevent cerebral diseases, such as epilepsy, and to protect the heart as well as inhibiting the release of TNF-α (tumor necrosis factor), an inflammation mediator, and the production of MIP-1α, interleukin-12 and interferon-γ, all acting as inflammation mediators. On the other hand, the inactivation of $A_3$ adenosine receptor causes the release of inflammation factors, such as histamine, from mast cells, bronchoconstriction, and the apoptosis of immune cells. Accordingly, $A_3$ adenosine antagonists have the possibility to be developed as anti-inflammatory agents and anti-asthmatics. Therefore, compounds with pharmacological selectivity are believed to be drugs useful in the treatment of various diseases, including asthma, inflammation, cerebral ischemia, heart diseases, cancer, etc.

The nucleoside based compounds $N^6$-(3-iodobenzyl)-5'-(N-methylcarbamoyl)-adenosine (IB-MECA) and $N^6$-(3-iodobenzyl)-2-chloro-5'-(N-methylcarbamoyl)-adenosine (CI-IB-MECA) are representative human adenosine $A_3$ agonists, and exhibit higher affinity and selectivity for the $A_3$ adenosine receptor than for the $A_1$ and $A_2$ adenosine receptors. On the other hand, most potent and selective human $A_3$ adenosine receptor antagonists possess non-purinergic heterocyclic skeleton compounds. However, nearly all of the non-purinergic heterocyclic human $A_3$ adenosine antagonists are found to induce weak or ineffective activity through rat $A_3$ adenosine receptor and thus were unsuitable for evaluation in small animal models, which is indispensable to the development of drugs for clinical application (Baraldi, P. G et al., Curr. Med. Chem., 12, 1319-1329, 2005). However, the nucleoside based compounds exhibit higher affinity and selectivity regardless of species than the non-purinergic based heterocyclic compound. Therefore, the nucleoside based compounds can be used in an animal experiment easily and it is believed that they can probably be developed as new drugs. Accordingly, it is necessary to develop the nucleoside based selective $A_3$ antagonist.

The present inventors analyzed various precedent studies and found that representative AB-MECA and Cl-IB-MECA must include N-methylcarbamoyl group at 5-position of sugar and 6-position of purin at a base must be substituted with arylamino group or alkylamino group in order to act as an agonist on an adenosine $A_3$ receptor. As N-methylcarbamoyl group at 5-position of sugar induces conformational change which is essential to agonistic action of receptor through hydrogen bonding (Kim, S-K. et al., J. Mol. Graph. Model., 25, 562-577, 2006), it is believed that they can be developed as $A_3$ receptor antagonist by synthesizing material in which N-methylcarbamoyl group at 5-position of sugar is eliminated.

Meanwhile, nonalcoholic steatohepatitis (NASH) or nonalcoholic fatty liver disease (NAFLD) is a disease caused not by alcohol but by obesity, diabetes, hyperlipidemia, drugs, etc.

Hepatocellular degeneration/necrosis resulting from the accumulation of fat in the hepatocytes causes inflammation and liver fibrosis, and the inflammation and the liver fibrosis cause NASH or NAFLD to develop into cirrhosis and liver cancer. Thus, NASH or NAFLD is recognized worldwide as a serious disease.

In this regard, the present inventors first studied an adenosine $A_3$ receptor antagonist as a preventive and therapeutic agent for NASH or NAFLD, liver fibrosis and liver cirrhosis. As a result, the present inventors have completed the present invention by synthesizing a novel adenosine derivative compound that has the activity of alleviating NASH or NAFLD and the effect of inhibiting fibrosis of liver tissue by inhibiting steatosis, inflammation and ballooning of liver tissue.

DISCLOSURE

Technical Problem

The present invention provides a pharmaceutical composition for preventing or treating liver diseases such as nonalcoholic steatohepatitis (NASH) or nonalcoholic fatty liver disease (NAFLD), liver fibrosis and liver cirrhosis, the pharmaceutical composition including an adenosine derivative acting as an adenosine $A_3$ receptor antagonist.

However, aspects of the inventive concept are not restricted to the one set forth herein. The above and other aspects of the inventive concept will become more apparent to one of ordinary skill in the art to which the inventive concept pertains by referencing the detailed description of the inventive concept given below.

Technical Solution

According to an aspect of the inventive concept, there is provided a pharmaceutical composition for preventing or treating liver disease. The pharmaceutical composition includes a compound represented by formula 1 below or a pharmaceutically acceptable salt of the compound as an active ingredient:

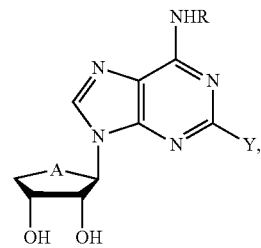

Formula 1 wherein A is S, R is a linear or branched $C_1$-$C_5$ alkyl which is non-substituted or is independently or selectively substituted with one or more $C_6$-$C_{10}$ aryl groups, a benzyl which is non-substituted or is independently or selectively substituted with halogen or one or more linear or branched $C_1$-$C_4$ alkoxy groups, or a hydroxycarbonyl-substituted benzyl, and Y is H or a halogen atom.

The liver disease is one or more of nonalcoholic steatohepatitis (NASH) or nonalcoholic fatty liver disease (NAFLD), liver fibrosis, and liver cirrhosis.

The formula 1 may be a compound represented by formula A below:

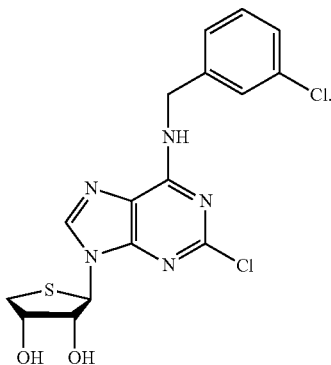

Formula A

According to another aspect of the inventive concept, there is provided an oral agent for preventing or treating liver disease. The oral agent includes a compound represented by formula 1 below or a pharmaceutically acceptable salt of the compound:

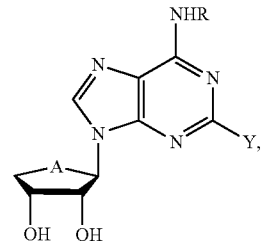

Formula 1 wherein A is S, R is a linear or branched $C_1$-$C_5$ alkyl which is non-substituted or is independently or selectively substituted with one or more $C_6$-$C_{10}$ aryl groups, a benzyl which is non-substituted or is independently or selectively substituted with halogen or one or more linear or branched $C_1$-$C_4$ alkoxy groups, or a hydroxycarbonyl-substituted benzyl, and Y is H or a halogen atom.

Also, a vehicle may include one or more of methyl cellulose (MC), dimethyl sulfoxide (DMSO), polyethylene glycol (PEG), and distilled water.

The compound represented by formula 1 or the pharmaceutically acceptable salt of the compound may be filled in a powder state in a capsule.

The liver disease is one or more of nonalcoholic steatohepatitis (NASH) or nonalcoholic fatty liver disease (NAFLD) and liver fibrosis.

The formula 1 may be a compound represented by formula A below:

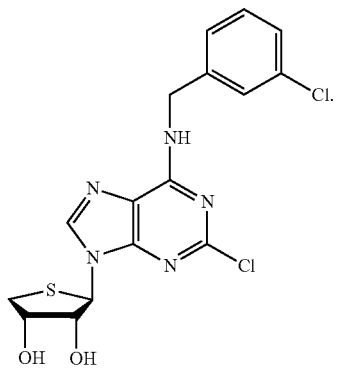

Formula A

Advantageous Effects

An adenosine derivative of the present invention can act as an adenosine $A_3$ receptor antagonist having the effect of alleviating nonalcoholic steatohepatitis (NASH) or nonalcoholic fatty liver disease (NAFLD), liver fibrosis and liver cirrhosis. In addition, the adenosine derivative is absorbed excellently when orally administered and is a biocompatible substance hardly toxic to the body. Therefore, the adenosine derivative can be used as a pharmaceutical composition highly suitable for prevention and treatment of liver disease.

However, the effects of embodiments of the inventive concept are not restricted to the one set forth herein. The above and other effects of the embodiments will become more apparent to one of daily skill in the art to which the embodiments pertain.

MODE FOR INVENTION

Figure 1:
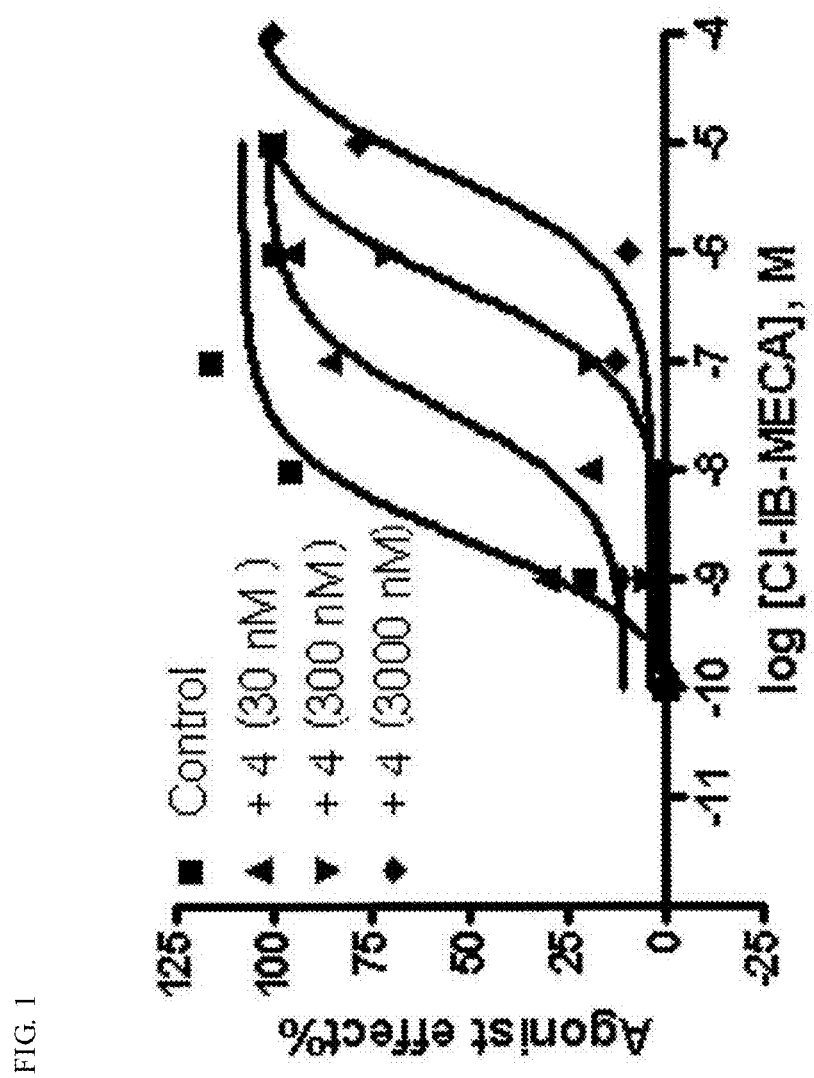
FIG. 1 is a graph showing the antagonist effect of the compound of Example 4 on the Chinese hamster ovary (CHO) cells treated with the agonist Cl-IB-MECA.

In accordance with an aspect thereof, the present invention pertains to an adenosine derivative compound represented by the following Chemical formula 1, or a pharmaceutically acceptable salt thereof as an active ingredient.

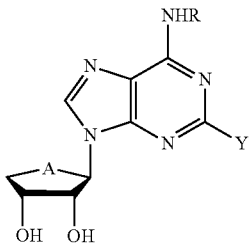

<Chemical formula 1> wherein,

A is O or S,

R is a linear or branched $C_1$~$C_5$ alkyl which is non-substituted or is independently or selectively substituted with one or more $C_6$~$C_{10}$ aryl groups, a benzyl which is non-substituted or is independently or selectively substituted with halogen or one or more linear or branched $C_1$~$C_4$ alkoxy groups, or a hydroxy carbonyl-substituted benzyl; and Y is H or a halogen atom.

In a preferable compound of Chemical formula 1,

A is O or S,

R is methyl, ethyl, propyl, naphthylmethyl, benzyl, benzyl independently or selectively substituted with a substituent selected from a group consisting of F, Cl, Br, I, $C_1$~$C_3$ alkoxy and combinations thereof, or toluic acid, and Y is H or Cl.

In a more preferable embodiment,
A is O or S,
R is methyl, ethyl, 1-naphthylmethyl, benzyl, 2-chlorobenzyl, 3-fluorobenzyl, 3-chlorobenzyl, 3-bromobenzyl, 3-iodobenzyl, 2-methoxy-5-chlorobenzyl, 2-methoxybenzyl, or 3-toluic acid, and
Y is H or Cl.

The adenosine derivatives according to a preferred embodiment of the present invention include:
1) (2R,3R,4S)-2-(2-chloro-6-(3-fluorobenzylamino)-9H-purin-9-yl)tetrahydrothiophen-3,4-diol;
2) (2R,3R,4S)-2-(2-chloro-6-(3-chlorobenzylamino)-9H-purin-9-yl)tetrahydrothiophen-3,4-diol;
3) (2R,3R,4S)-2-(6-(3-bromobenzylamino)-2-chloro-9H-purin-9-yl)tetrahydrothiophen-3,4-diol;
4) (2R,3R,4S)-2-(2-chloro-6-(3-iodobenzylamino)-9H-purin-9-yl)tetrahydrothiophen-3,4-diol;
5) (2R,3R,4S)-2-(2-chloro-6-(2-chlorobenzylamino)-9H-purin-9-yl)tetrahydrothiophen-3,4-diol;
6) (2R,3R,4S)-2-(2-chloro-6-(5-chloro-2-methoxybenzylamino)-9H-purin-9-yl)tetrahydrothiophen-3,4-diol;
7) (2R,3R,4S)-2-(2-chloro-6-(2-methoxybenzylamino)-9H-purin-9-yl)tetrahydrothiophen-3,4-diol;
8) (2R,3R,4S)-2-(2-chloro-6-(naphthalen-1-ylmethylamino)-9H-purin-9-yl)tetrahydrothiophen-3,4-diol;
9) 3-((2-chloro-9-((2R,3R,4S)-3,4-dihydroxytetrahydrothiophen-2-yl)-9H-purine-6-ylamino)methyl)benzoic acid;
10) 2-(2-chloro-6-methylamino-purin-9-yl)tetrahydrothiophen-3,4-diol;
11) (2R,3R,4S)-2-(6-(3-fluorobenzylamino)-9H-purin-9-yl)tetrahydrothiophen-3,4-diol;
12) (2R,3R,4S)-2-(6-(3-chlorobenzylamino)-9H-purin-9-yl)tetrahydrothiophen-3,4-diol;
13) (2R,3R,4S)-2-(6-(3-bromobenzylamino)-9H=purin-9-yl)tetrahydrothiophen-3,4-diol;
14) (2R,3R,4S)-2-(6-(3-iodobenzylamino)-9H-purin-9-yl)tetrahydrothiophen-3,4-diol;
15) (2R,3R,4R)-2-(6-(3-bromobenzylamino)-2-chloro-9H-purin-9-yl)tetrahydrofuran-3,4-diol; and
16) (2R,3R,4R)-2-(2-chloro-6-(3-iodobenzylamino)-9H-purin-9-yl)tetrahydrofuran-3,4-diol.

The adenosine derivative, represented by Chemical formula 1, in accordance with the present invention may be in the form of pharmaceutically acceptable salts. Useful are acid addition salts formed with a variety of pharmaceutically acceptable organic acids or inorganic acids. Examples of suitable organic acids include carboxylic acid, phosphoric acid, sulfonic acid, acetic acid, propionic acid, octanoic acid, decanic acid, glycolic acid, lactic acid, fumaric acid, succinic acid, adipic acid, malic acid, tartaric acid, citric acid, glutamic acid, aspartic acid, maleic acid, benzoic acid, salicylic acid, phthalic acid, phenylacetic acid, benzene sulfonic acid, 2-naphthalene sulfonic acid, methyl sulfonic acid, ethyl sulfonic acid, and dodecyl sulfonic acid. Suitable inorganic acids may be exemplified by hydrochloric acid, sulfuric acid, halogen acid, and phosphoric acid.

The adenosine derivatives represented by Chemical formula 1 can include not only pharmaceutically acceptable salts, but also all salts, hydrates and solvates which can be prepared using conventional methods.

In accordance with another aspect thereof, the present invention pertains to a method for preparing the adenosine derivative represented by Chemical formula 1.

In detail, the adenosine derivative may be synthesized according to the following Reaction formula 1.

The method includes reacting a compound of Chemical formula 2 with a silylated purine compound in the presence of a Lewis acid catalyst to produce a β-anomer compound of Chemical formula 3 (Step 1); adding hydrochloric acid to the β-anomer compound of Chemical formula 3 to produce a diol compound of Chemical formula 4 (Step 2); and reacting the diol compound of Chemical formula 4 with an amine compound in the presence of a base as a catalyst to produce the adenosine derivative (Step 3).

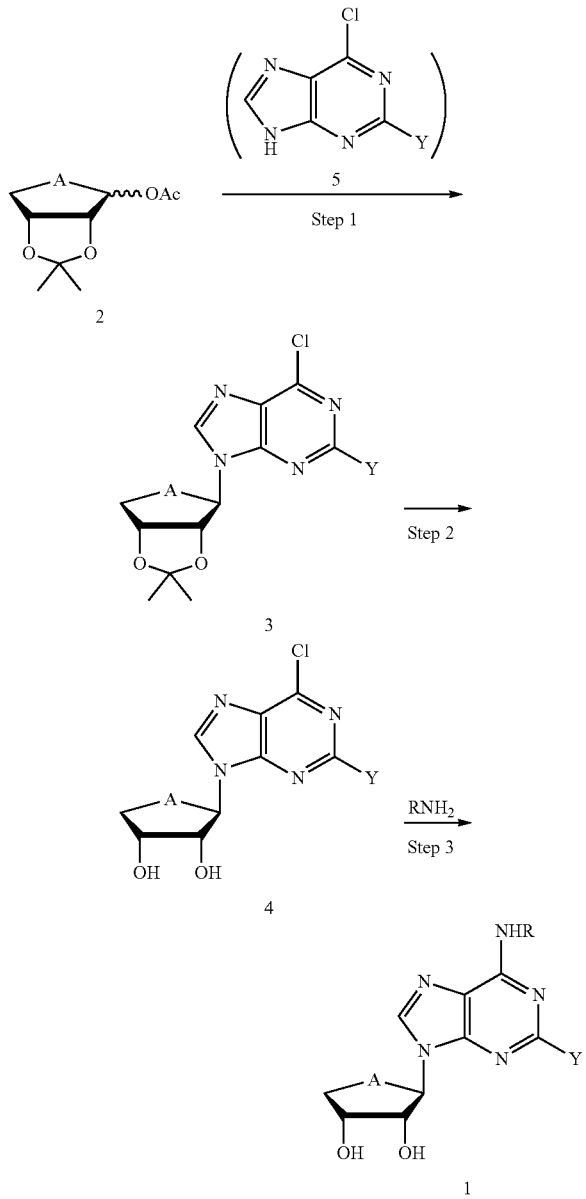

<Reaction formula 1>

In Reaction formula 1, A, R and Y are as defined in Chemical formula 1.

The synthesis will be explained in detail by each step.

In Step 1, the synthesis of the adenosine derivative starts with the compound of Chemical formula 2. In the presence of a Lewis acid as a catalyst, this starting material is reacted with a silylated purine compound to give the β-anomer compound of Chemical formula 3. Trimethylsilyl trifluoromethanesulfonate (TMSOTf) may be used as the Lewis acid catalyst. Dichloroethane, chloroform, acetonitrile, or dichloromethane is preferably used as the solvent in Step 1, with higher preference for dichloroethane. The silylated purine compound can be obtained by reaction between the purine compound of Chemical formula 5 and hexamethyldisilazane (HMDS) in the presence of ammonium sulfate as a catalyst.

In Step 2, HCl is added to the compound of Chemical formula 3 obtained in Step 1 to obtain a diol compound of Chemical formula 4. Instead of HCl, acetic acid, sulfuric acid or p-toluene sulfonic acid may be used.

In Step 3, the diol compound of Chemical formula 4 obtained in Step 2 is reacted with an amine compound in the presence of a base as a catalyst to give the adenosine derivative.

Examples of the base catalyst in Step 3 include triethylamine, pyridine, N,N-dimethylaminopyridine, and 1,4-dioxane with preference for triethylamine. In addition, the reaction may be preferably conducted in a solvent selected from among lower alcohols such as methanol and ethanol, 1,4-dioxane, tetrahydrofuran and chloroform.

Depending on the kinds of the substituent A, the compound of Chemical formula 2 used as the starting material for the synthesis of the adenosine derivative according to the present invention may be synthesized through the reaction route of either Reaction formula 2 or 3.

When the substituent A is sulfur (S), as seen in Reaction formula 2 below, the synthesis of the starting material is accomplished by reacting the D-mannose compound of Chemical formula 6 with 2,2-dimethoxypropane in the presence of an acid as a catalyst to give the diacetonide compound of Chemical formula 7 (Step $a_1$); opening the compound of Chemical formula 7 obtained in Step $a_1$ in the presence of a reducing agent to afford the diol compound of Chemical formula 8 (Step $a_2$); mesylating the diol compound of Chemical formula 8 obtained in Step $a_2$ to afford the dimesyl compound of Chemical formula 9 (Step $a_3$); cyclizing the compound of Chemical formula 9 obtained in Step $a_3$ to afford the thiosugar compound of Chemical formula 10 (Step $a_4$); selectively hydrolyzing the compound of Chemical formula 10 obtained in Step $a_4$ to afford the diol compound of Chemical formula 11 (Step $a_5$); and converting the compound of Chemical formula 11 obtained in Step $a_5$ into an acetate compound of Chemical formula 2a in the presence of a catalyst (Step $a_6$).

<Reaction formula 2>

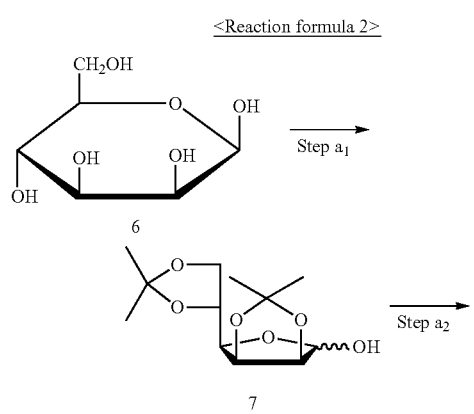

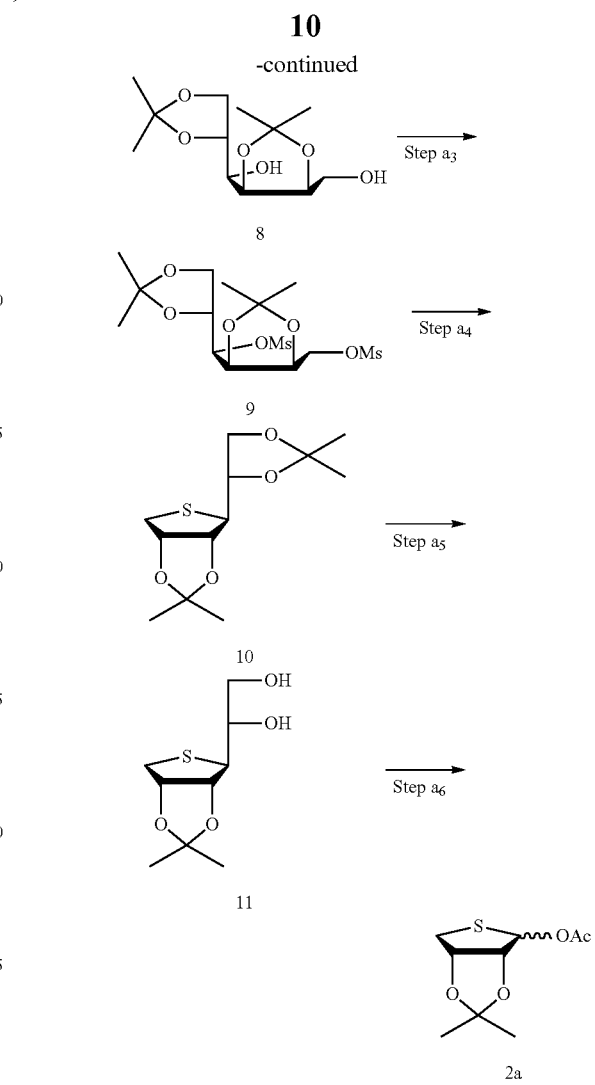

In Reaction formula 2, Compound 2a is the compound of Chemical formula 2.

Below, the synthesis of Compound 2a will be further explained in detail by each step.

As in Step $a_1$, the synthesis of Compound 2 starts from the D-mannose of Chemical formula 6. D-Mannose is reacted with 2,2-dimethoxypropane in the presence of an acid as a catalyst to give diacetonide compound of Chemical formula 7.

An acid in combination with anhydrous acetic acid, functioning to catalyze the conversion of D-mannose of Chemical formula 6 into the compound of Chemical formula 7, may be an inorganic acid, such as conc. sulfuric acid or hydrochloric acid, or an organic acid, such as p-toluenesulfonic acid.

In Step $a_2$, the compound of Chemical formula 7 is ring-opened in the presence of a reducing agent to afford the diol compound of Chemical formula 8.

The treatment of the compound of Chemical formula 7 with the reducing agent sodium borohydride produces the compound of Chemical formula 8. In lieu of sodium borohydride, a metal hydride, such as lithium aluminum hydride, or sodium sulfite may be used.

In Step $a_3$, the compound of Chemical formula 8 obtained in Step $a_2$ is mesylated into the dimesyl compound of Chemical formula 9.

The compound of Chemical formula 9 can be obtained by reacting the compound of Chemical formula 8 with methanesulfonylchloride (MsCl). In this case, an inert solvent, such as, ethyl ether, petroleum ether, dichloromethane, tetrahydrofuran and N,N-dimethylformamideformamide, can be used as solvent for the reaction.

In Step $a_4$, the compound of Chemical formula 9 obtained in Step $a_3$ is cyclized into a thiosugar compound of Chemical formula 10.

The compound of Chemical formula 10 can be obtained by reacting the compound of Chemical formula 9 with sodium sulfide. Alternatively, the compound of Chemical formula 10 can be achieved by substitution with a thio ester, such as methyl thioacetate, followed by reaction with sodium alkoxide. N,N-dimethylformamide or dimethylsulfoxide may be used as the solvent for Step $a_4$.

In Step $a_5$, the compound of Chemical formula 10 obtained in Step $a_4$ is selectively hydrolyzed into the diol compound of Chemical formula 11.

By having selective hydrolysis of 5,6-acetonide, the compound of Chemical formula 11 can be obtained from the compound of Chemical formula 10 by using acetic acid. In place of acetic acid, sulfuric acid, hydrochloric acid or p-toluene sulfonic acid may be used.

In Step $a_6$, the compound of Chemical formula 11 obtained in Step $a_5$ is converted into the acetate compound of Chemical formula 2a in the presence of a catalyst.

Conversion into the compound of the Chemical formula 2a is accomplished by reacting the compound of Chemical formula 11 with lead tetraacetate (Pd(OAc)$_4$).

When the substituent A is oxygen (O), Reaction formula 3 is taken for the synthesis of the starting material 2. As seen in Reaction formula 3, the synthesis of the starting material is accomplished by reacting the compound of Chemical formula 12 with a reducing agent to afford the lactol compound of Chemical formula 13 (Step $b_1$); and reacting the compound of Chemical formula 13 obtained in Step $b_1$ with anhydrous acetic acid to afford an acetate compound of Chemical formula 2b (Step $b_2$).

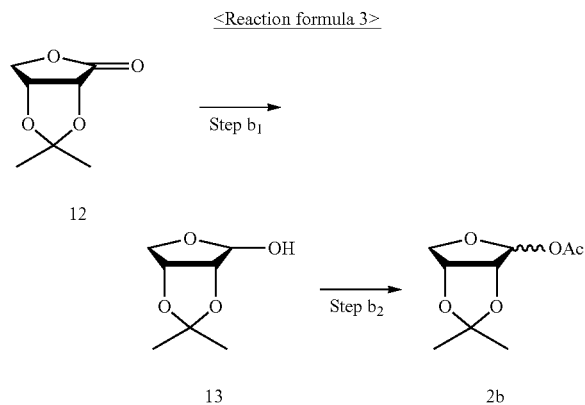

<Reaction formula 3>

In Reaction formula 3, Compound 2b is the compound of Chemical formula 2.

Below, the synthesis of Compound 2b will be further explained in detail by each step.

In Step $b_1$, the compound of Chemical formula 12 is reduced into the lactol compound of Chemical formula 13.

For the reduction of the compound of Chemical formula 12, an easily synthesizable compound, into the compound of Chemical formula 13, diisobutylaluminium hydride (DIBAL) may be used as a catalyst.

In Step $b_2$, the compound of Chemical formula 13 is reacted with anhydrous acetate to afford the acetate compound of Chemical formula 2b.

Thus, the compound of Chemical formula 2b can be obtained by reacting the lactol compound of Chemical formula 13 with acetate.

In accordance with a further aspect thereof, the present invention pertains to an $A_3$ adenosine receptor antagonist having the adenosine derivative represented by Chemical formula 1 or a pharmaceutically acceptable salt thereof as an active ingredient.

In accordance with still a further aspect thereof, the present invention pertains to a pharmaceutical composition for the prevention and treatment of inflammatory diseases, having the adenosine derivative represented by Chemical formula 1 or a pharmaceutically acceptable salt thereof as an active ingredient.

When expressed in Chinese Hamster Ovary (CHO) cells, $A_3$ adenosine receptors were found to inhibit adenylyl cyclase, an enzyme that produces cAMP from ATP. Also, when activated by agonists, the $A_3$ adenosine receptor was proven to mediate the activation of guanosine triphosphate-dependent phospholipase C, an enzyme which catalyzes the degradation of phosphatidyl inositol into inositol triphosphate and DAG in the brain (Ramkumar, V. et al., J. Biol. Chem., 268, 168871-168890, 1993; Abbracchio, M. P. et al., Mol. Pharmacol., 48, 1038-1045, 1995). These findings account for the possibility that there is a reaction pathway mediated by the $A_3$ adenosine receptor in cerebral ischemia when it is activated because this second messenger system serves as a reaction pathway for nerve injury in cerebral ischemia. Also, $A_3$ receptor agonists are known to prevent cerebral diseases, such as epilepsy, and to protect the heart as well as inhibiting the release of TNF-α (tumor necrosis factor), an inflammation mediator, and the production of MIP-1α, interleukin-12 and interferon-γ, all of which act as inflammation mediators. On the other hand, the inactivation of $A_3$ adenosine receptor causes the release of inflammation factors, such as histamine, from mast cells, bronchoconstriction, and the apoptosis of immune cells. Accordingly, $A_3$ adenosine antagonists have the possibility of being candidates as anti-inflammatory agents and anti-asthmatics.

The adenosine derivatives of the present invention were assayed for human adenosine receptor (hAR)-binding affinity and selectivity. In an assay for binding affinity (refer to Experimental Example 1), the adenosine derivatives of the present invention were found to have high binding affinity for human $A_3$ adenosine receptors (h$A_3$ AR), but low affinity for $A_1$ and $A_{2A}$ adenosine receptors, thereby showing high selectivity. Particularly, the compound of Example 12 shows the highest binding affinity for h$A_3$ AR with $K_i$ determined at 1.50±0.40 nM, followed by the compound of Example 2 ($K_i$=1.66±0.90 nM), the compound of Example 14 ($K_i$=2.50±1.00 nM), the compound of Example 10 ($K_i$=3.69±0.25 nM) and the compound of Example 4 ($K_i$=4.16±0.50 nM) in decreasing order of binding affinity. Also, the compound of Example 4 was measured to have high binding affinity for the rat $A_3$ adenosine receptor expressed in CHO cells ($K_{2 1}$=3.89±1.15 nM). In addition, the compounds of Examples 15 and 16, both adenosine derivatives in the form of 4'-O oxonucleoside, show high binding affinity and selectivity (see, Table 1).

In assays for anti-inflammatory activity (see, Experimental Examples 3-6), the adenosine derivatives of the present invention were found to have anti-inflammatory activity, although this was low compared to that of the control hydrocortisone.

Figure 2:
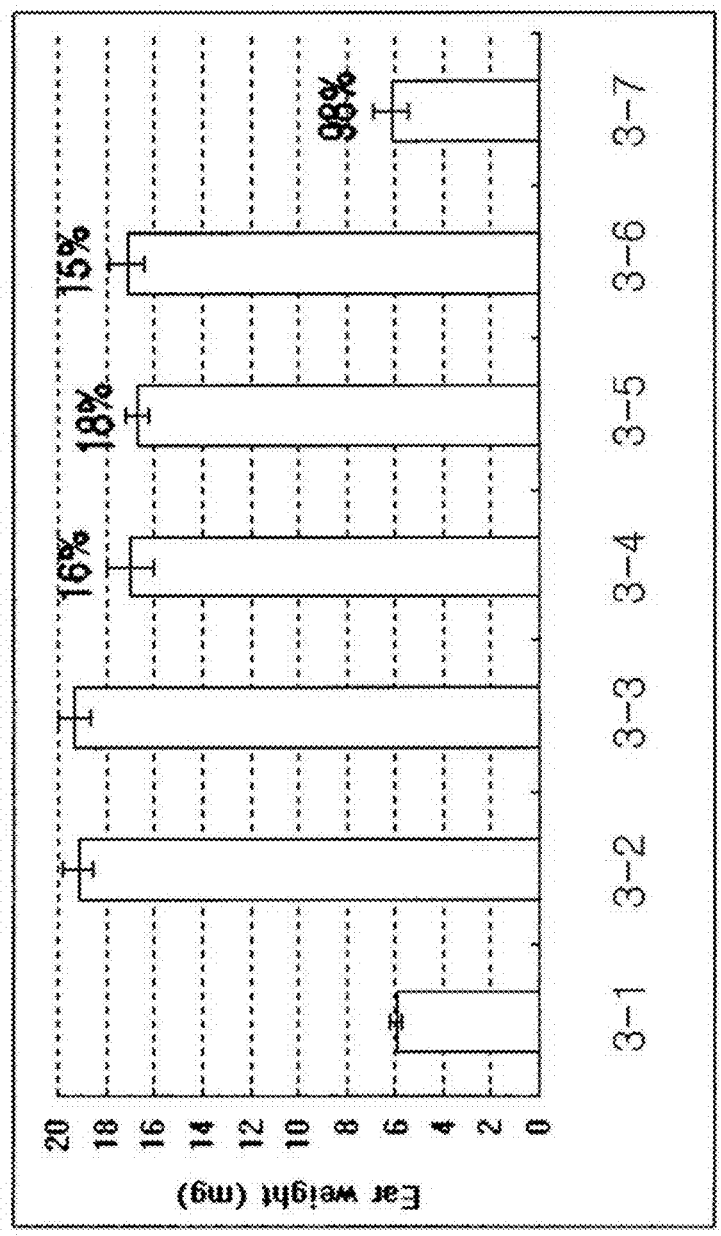
FIG. 2 is a graph showing the anti-inflammatory activity of the compounds (Examples 2, 3 and 4) of the present invention in animal tests.

When administered to mice treated with TPA in the ears, the compounds of Examples 2 to 4, diluted in acetone, were observed to decrease inflammation of the ears to some degree (see, FIG. 2). In addition, the compounds of Examples 1 and 6 were found to have anti-inflammatory activity four or more times that of the compounds of Examples 2 to 4, as measured on the basis of inhibition percentage (see, FIG. 3).

Figure 4:
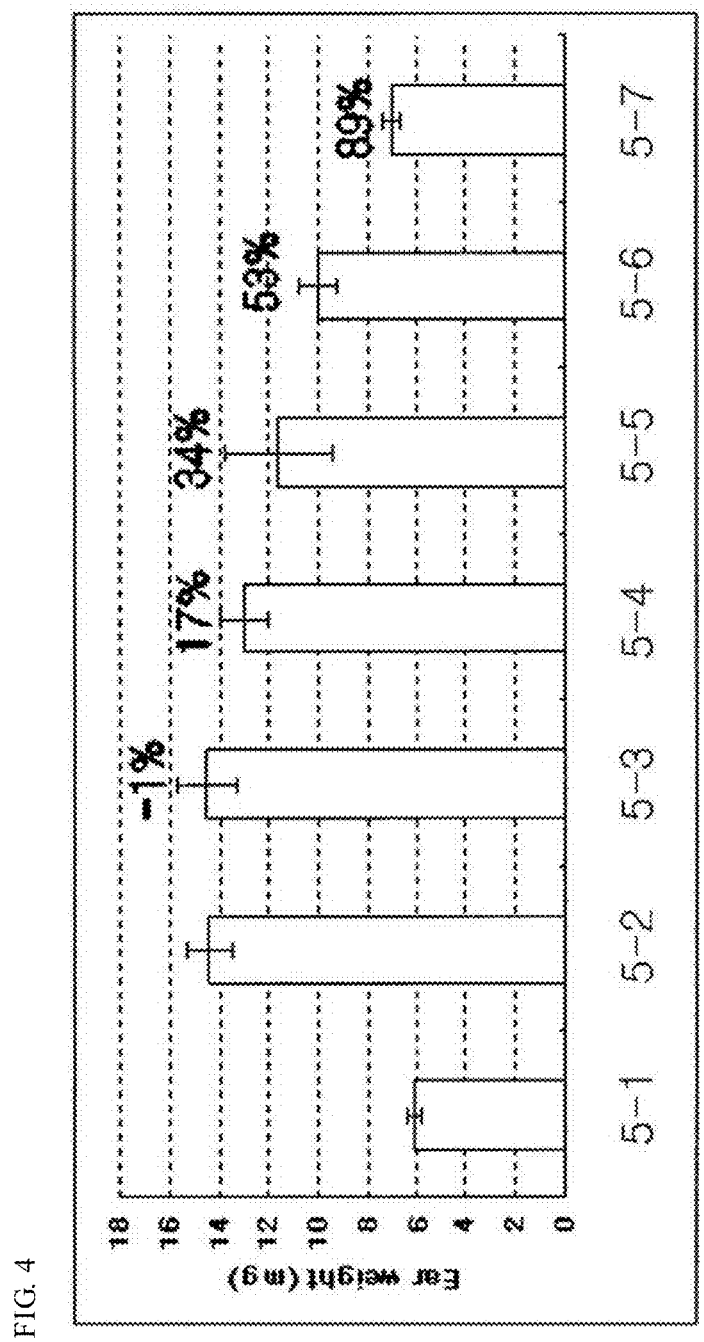
FIG. 4 is a graph showing the anti-inflammatory activity of the compounds (Examples 5, 7 and 8) of the present invention in animal tests.

In an assay for anti-inflammatory activity, the compounds of Examples 5-7, diluted at a concentration of 0.5% in a mixture of distilled water and acetone (1:4), were measured to have percentages of inflammation inhibition of 17%, 34% and 53%, respectively (see, FIG. 4). The compounds of Examples 15 and 16, diluted at a concentration of 0.5% in a mixture of DMSO and acetone (1:9), were measured to have percentages of inflammation inhibition of 59% and 79%, respectively (see, FIG. 5). Based on the observations in the assay, the adenosine derivatives of the present invention were proven to have anti-inflammatory activity.

Having high binding affinity and selectivity for $A_3$ adenosine receptors, thus, the adenosine derivatives, represented by Chemical formula 1, according to the present invention, can be effectively used as $A_3$ adenosine receptor antagonists. Further, the adenosine derivatives of the present invention exert antagonism on $A_3$ adenosine receptors, showing anti-inflammatory activity, and thus are useful in the prevention and treatment of inflammatory diseases.

The inflammatory diseases to which the adenosine derivatives of the present invention can be effectively applied include acute and chronic inflammatory diseases, such as ulcerative inflammation, exudative inflammation, purulent inflammation, hemorrhagic inflammation, and hyperplastic inflammation.

With regard to pharmaceutical compositions having the adenosine derivative of the present invention or pharmaceutically acceptable salts thereof, they are formulated into dosage forms with expedients, as will be explained with the following examples, which are illustrative only, and are not intended to limit the present invention. The compositions of the present invention may be administered systemically or topically.

The compound of the present invention may be clinically administered in oral or non-oral forms. It is usually formulated in combination with a diluent or excipient, such as, a filler, a thickening agent, a binder, a wetting agent, a disintegrant, a surfactant, etc. Solid agents intended for oral administration of the compound of the present invention may be in the form of tablets, pills, powders, granules, capsules, and the like. These solid agents are formulated in combination with at least one excipient such as starch, calcium carbonate, sucrose, lactose, or gelatine. Besides, a lubricant, such as magnesium stearate, talc and the like, may be added, as well. Liquid agents intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be contained in the liquid agents for the oral administration of the compound of the present invention.

Also, non-oral dosage forms of the compound of the present invention include injections, emulsions, inhalations, and suppositories. For injections, sterile aqueous solutions, non-aqueous solvents, and suspensions made from propylene glycol, polyethylene glycol, vegetable oils such as olive oil, and esters such as ethyl oleate may be used. The basic materials of suppositories include witepsol, macrogol, tween 61, cacao butter, laurin oil, glycerol, and gelatine. The compound of the present invention may be formulated into ointments or cream for topical application.

Depending on the conditions of patients, including age, body weight, sex, administration route, and disease severity, the administration dose of the compound of the present invention to humans may vary. Typically, the compound of the present invention is administered at a dose from 0.001 to 100 mg/kg of body weight a day and preferably at a dose from 0.01 to 30 mg/kg of body weight a day. The compound may be administered in a single dose or in divided doses per day. The compound of the present invention is contained in an amount from 0.0001 to 10 wt % based on the total weight of the composition and preferably in an amount from 0.001 to 1 wt %. Also, the administration route is dependent on patient's health state and disease severity.

The present invention provides a pharmaceutical composition for preventing and/or treating liver disease, the pharmaceutical composition containing an adenosine derivative, which includes the compound represented by Chemical formula 1 above and/or the pharmaceutically acceptable salt of the compound, as an active ingredient.

Liver diseases may include all diseases, conditions and symptoms including nonalcholic steatohepatitis (NASH) or nonalcoholic fatty liver disease (NAFLD), liver fibrosis, and liver cirrhosis.

A preferred example of the adenosine derivative represented by the above Chemical formula 1 may be (2R,3R,4S)-2-(2-chloro-6-(3-chlorobenzylamino)-9H-purine-9-yl) tetrahydrothiophene-3,4-diol which is a compound represented by Chemical formula A below:

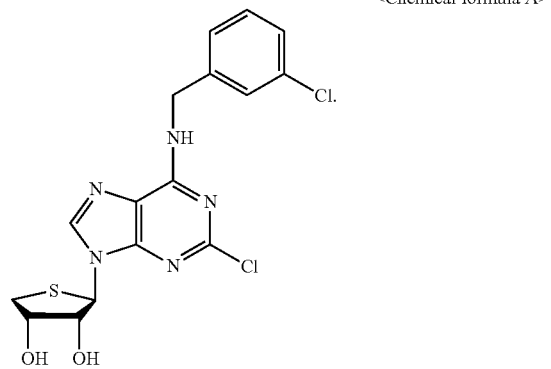

<Chemical formula A>

The pharmaceutical composition for preventing and/or treating liver disease according to the inventive concept can be formulated as an oral agent.

The oral agent may include the compound represented by the above formula 1 and/or the pharmaceutically acceptable salt of the compound and a vehicle. The vehicle may include one or more of methyl cellulose (MC), dimethyl sulfoxide (DMSO), polyethylene glycol (PEG), distilled water (DW), and a capsule. A preferred example of the vehicle may be 0.5 wt % methyl cellulose.

The oral agent may be a capsule that contains the compound represented by the above formula 1 and/or the pharmaceutically acceptable salt of the compound in a powder state or in the state of a solution dissolved in the vehicle.

The pharmaceutical composition for preventing and/or treating liver disease according to the inventive concept can be orally administered to a patient. A preferred dosage may be appropriately selected in consideration of a number of factors such as the condition and weight of the patient, the degree of disease, the drug form, and the route and duration of administration.

The adenosine derivative of the inventive concept can act as an adenosine $A_3$ antagonist that dose-dependently alleviates NASH or NAFLD, liver fibrosis and liver cirrhosis (see, Experimental Example 9). The adenosine derivative is excellent in blood concentration and stability when orally administered (see, Experimental Example 10) and is a biocompatible substance hardly toxic to the body (see, Experimental Examples 11 through 16). Therefore, the adenosine derivative can be used as a pharmaceutical composition highly suitable for prevention and/or treatment of liver disease.

Synthesis of the Starting Material

Preparation Example 1

Preparation of (3 aR,4R,6aS)-2,2-dimethyltetrahydrothieno[3,4-d][1,3]dioxol-4-yl acetate Step $a_1$. Preparation of (3aR,4R,6R,6aR)-6-(2,2-dimethyl-1,3-dioxolan-4-yl)-2,2-dimethyl-tetrahydrofuro[3,4-d][1,3]dioxol-4-ol To acetone (50 ml) were added D-mannose (1.74 g, 6.52 mmol) and 2,2-dimethoxypropane (2.45 ml, 19.55 mmol) with stirring, followed by cooling the solution to 0° C. To the solution was dropwise added conc. sulfuric acid (0.45 g, 1.96 mmol). The resulting reaction mixture was stirred at room temperature for 24 hrs, followed by neutralization with triethylamine and concentration in a vacuum. The concentrate was purified by silica gel column chromatography using a mixture of hexane:ethyl acetate (1:1, v/v) as an elution solvent to afford the object compound as a white solid (1.61 g, 95%).

m.p. 120.3-120.5° C.
$^1$H-NMR (CDCl$_3$) δ 5.34 (s, 1H), 4.76-4.79 (m, 1H), 4.58 (d, 1H, J=6.0 Hz), 4.34-4.39 (m, 1H), 4.15 (dd, 1H, J=3.6, 7.2 Hz), 4.00-4.08 (m, 2H);
$[α]^{25}_D$ 11.71 (c 0.11, CH$_2$Cl$_2$);
FAB-MS m/z 261 [M+H]$^+$.

Step $a_2$. Preparation of (1R)-(2,2-dimethyl-1,3-dioxolan-4-yl)((4R,5S)-5-(hydroxymethyl)-2,2-dimethyl-1,3-dioxolan-4-yl)methanol (3aR,4R,6R,6aR)-6-(2,2-dimethyl-1,3-dioxolan-4-yl)-2,2-dimethyl-tetrahydrofuro[3,4-d][1,3]dioxol-4-ol (1.50 g, 5.76 mmol), prepared in Step $a_1$, was carefully added to ethanol (25 ml) and the solution was cooled to 0° C. To the solution was added sodium borohydride (NaHB$_4$, 440 mg, 11.53 mmol), followed by stirring the solution at room temperature for 2 hrs. The reaction mixture was neutralized with acetic acid and concentrated in a vacuum. The concentrate was extracted with ethyl acetate and water. The organic layer was dried over anhydrous magnesium sulfate (MgSO$_4$), filtered and concentrated in a vacuum. The concentrate was purified by silica gel column chromatography using a mixture of hexane:ethyl acetate (1:1, v/v) as an elution solvent to afford the object compound in a syrup form (1.38 g, 92%).

$^1$H-NMR (CDCl$_3$) δ 4.33 (dd, 1H, J=1.6, 7.2 Hz), 4.24-4.28 (m, 1H), 4.06-4.13 (m, 2H), 3.92-3.97 (m, 1H), 3.76-3.85 (m, 2H), 3.59-3.61 (m, 1H), 1.48 (s, 3H), 1.38 (s, 3H), 1.36 (s, 3H), 1.33 (s, 3H);
$[α]^{25}_D$ -3.88 (c 0.44, CH$_2$Cl$_2$);
FAB-MS m/z 263 [M+H]+.

Step $a_3$. Preparation of (1R)-(2,2-dimethyl-1,3-dioxolan-4-yl)((4S,5S)-2,2-dimethyl-5-((methylsulfonyloxy)methyl)-1,3-dioxolan-4-yl)methylmethanesulfonate (1R)-(2,2-dimethyl-1,3-dioxolan-4-yl)((4R,5 S)-5-hydroxymethyl)-2,2-dimethyl-1,3-dioxolan4-yl)methanol (38.52 g, 146.85 mmol), prepared in Step $a_2$, and 4-dimethylaminopyridine (4-DMAP, 5.38 mg, 44.06 mmol) were added to a mixture of dichloromethane (300 ml) and triethylamine (163.75 ml, 1.17 mol), and the solution was stirred and cooled to 0° C. To this was dropwise added dimethanesulfonyl chloride (47.59 ml, 587.42 mmol). After stirring at room temperature for 1 hr, the reaction mixture was extracted with dichloromethane and washed with a saturated sodium hydrogen carbonate (NaHCO$_3$) solution. The organic layer thus obtained was dried over anhydrous magnesium sulfate (MgSO$_4$), filtered and concentrated in a vacuum. The dimesyl compound thus produced, having the form of a brown syrup, was purified through silica gel column chromatography using a mixture of hexane:ethylacetate (5:1, v/v) as an elution solvent to afford the object compound in syrup form (57.83 g, 94%).

$^1$H-NMR (CDCl$_3$) δ 4.75 (pseudo t, 1H, J=7.4 Hz), 4.33-4.45 (m, 4H), 4.06-4.20 (m, 3H), 3.12 (s, 3H), 3.07 (s, 3H), 1.51 (s, 3H), 1.43 (s, 3H), 1.37 (s, 3H), 1.33 (s, 3H);
$[α]^{25}_D$ 38.32 (c 0.29, CH$_2$Cl$_2$);
FAB-MS m/z 419 [M+H]+.

Step $a_4$. Preparation of (3aR,4S,6aS)-4-(2,2-dimethyl-1,3-dioxolan-4-yl)-2,2-dimethyltetrahydrothieno[3,4-d][1,3]dioxol (1R)-(2,2-dimethyl-1,3-dioxolan-4-yl)((4S,5 S)-2,2-dimethyl-5-((methylsulfonyloxy)methyl)-1,3-dioxolan-4-yl)methylmethanesulfonate (993.80 g, 2.23 mmol), prepared in Step $a_3$, was dissolved in DMF (50 ml). Following the addition of sodium sulfide (348.30 g, 4.46 mmol) thereto, the solution was stirred at 80° C. under a reflux condition overnight. Thereafter, the solvent was removed in a vacuum and the residue was extracted with ethyl acetate and water. The organic layer was dried over anhydrous magnesium sulfate (MgSO$_4$), filtered, and concentrated in a vacuum. The concentrate was purified through silica gel column chromatography using a mixture of hexane:ethyl acetate (8:1, v/v) as an elution solvent to afford the object compound in a syrup form (453.0 mg, 78%).

$^1$H-NMR (CDCl$_3$) δ 4.92 (dt, 1H, J=1.8, 5.6 Hz), 4.72 (dd, 1H, J=2.0, 6.0 Hz), 4.26-4.30 (m, 1H), 4.04 (s, 1H), 3.79 (t, 1H, J=3.8 Hz), 3.31-3.32 (m, 1H), 3.19 (dd, 1H, J=5.4, 12.0 Hz), 2.84 (dd, 1H, J=1.6, 12.0 Hz), 1.51 (s, 3H), 1.43 (s, 3H), 1.32 (dd, 6H, J=8.4 Hz);
$[α]^{25}_D$ -96.04 (c 0.20, CH$_2$Cl$_2$);
FAB-MS m/z 261 [M+H]+.

Step $a_5$. Preparation of 1-((3 aR,4S,6aS)-2,2-dimethyltetrahydrothieno[3,4-d][1,3]dioxol-4-yl)ethan-1,2-diol (3aR,4S,6aS)-4-(2,2-dimethyl-1,3-dioxolan-4-yl)-2,2-dimethyltetrahydrothieno[3,4-d][1,3]dioxol (21.78 g, 83.66 mmol), prepared in Step a$_4$, was dissolved in a 60% aqueous acetic acid solution (250 ml), followed by stirring the solution at room temperature for 2 hrs. The reaction mixture was concentrated in a vacuum and the concentrate was purified through silica gel column chromatography using a mixture of hexane:ethyl acetate (1:2, v/v) as an elution solvent to afford the object compound as a white solid (14.85 g, 81%).

$^1$H-NMR (CDCl$_3$) δ 4.92 (dt, 1H, J=1.8, 5.6 Hz), 4.72 (dd, 1H, J=2.0, 6.0 Hz), 4.26-4.30 (m, 1H), 4.04 (s, 1H), 3.79 (t, 1H, J=3.8 Hz), 3.31-3.32 (m, 1H), 3.19 (dd, 1H, J=5.4, 12.0 Hz), 2.84 (dd, 1H, J=1.6, 12.0 Hz), 1.51 (s, 3H), 1.43 (s, 3H), 1.32 (dd, 6H, J=8.4 Hz);

$[α]^{25}_D$-96.04 (c 0.20, CH$_2$Cl$_2$);

FAB-MS m/z 261 [M+H]$^+$.

Step a$_6$. Preparation of (3aR,4R,6aS)-2,2-dimethyl-tetrahydrothieno[3,4-d][1,3]dioxol-4-yl acetate 1-((3aR,4S,6aS)-2,2-dimethyltetrahydrothieno[3,4-d][1,3]dioxol-4-yl)ethan-1,2-diol (14.85 g, 67.41 mmol), prepared in Step a$_5$, was dissolved in ethyl acetate (300 ml) and cooled to 0° C. To the solution was added lead tetraacetate (Pb(OAc)$_4$, 157.31 g, 337.06 mmol), followed by stirring at room temperature overnight. The reaction mixture was filtered through a Celite filter and the filtrate was diluted in ethyl acetate. The organic layer was diluted in dichloromethane, washed with a saturated aqueous sodium hydrogen carbonate (NaHCO$_3$) solution, dried over anhydrous magnesium sulfate, and concentrated in a vacuum. The concentrate was purified through silica gel column chromatography using a mixture of hexane:ethyl acetate (8:1, v/v) as an elution solvent to afford the object compound in a syrup form (8.82 g, 60%).

$^1$H-NMR (CDCl$_3$) δ 5.03 (dd, 1H, J=5.6, 9.6 Hz), 4.79 (dd, 1H, J=5.6, 8.8 Hz), 3.21-3.27 (m, 2H), 3.01 (dt, 2H, J=0.8, 12.8 Hz), 2.05 (s, 3H), 1.50 (s, 3H), 1.31 (s, 3H);

$[α]^{25}_D$-258.15 (c 0.18, CH$_2$Cl$_2$);

FAB-MS m/z 218 [M]$^+$.

Preparation Example 2

Preparation of (3aS,4S,6aS)-2,2-Dimethyl-tetrahydrofuro[3,4-d][1,3]dioxol-4-yl acetate Step b$_1$. Preparation (3aR,4R,6aR)-2,2-dimethyl-tetrahydrofuro[3,4-d][1,3]dioxol-4-ol 2,3-O-isopropylidene-D-erythronolactone (1.04 g, 6.42 mmol) was dissolved in toluene (20 ml), followed by the addition of 1 M diisobutylaluminium hydride (DIBAL)/THF to the solution at −78° C. The reaction mixture was stirred at the same temperature for 30 min and methanol was slowly added until the reaction terminated. The suspension was filtered through a Celite filter and the filtrate was extracted with ethyl acetate and water, followed by silica gel column chromatography using a mixture of hexane:ethyl acetate (3:1, v/v) to give the object compound in syrup form (1.94 g, 96%).

$^1$H-NMR (CDCl$_3$) δ 5.39 (s, 1H), 4.82 (dd, 1H, J=3.6, 6.0 Hz), 4.55 (d, 1H, J=6.0 Hz), 4.05 (dd, 1H, J=3.6, 10.2 Hz), 4.00 (d, 1H, J=10.0 Hz), 1.45 (s, 3H), 1.30 (s, 3H).

Step b$_2$. Preparation of (3aS,4S,6aS)-2,2-dimethyl-tetrahydrofuro[3,4-d][1,3]dioxol-4-yl acetate The lactol compound (875.9 mg, 5.47 mmol) prepared in Step b$_1$ was dissolved in pyridine (10 ml), followed by the addition of anhydrous acetic acid (0.67 ml, 6.56 mmol) at 0° C. The reaction mixture was stirred at room temperature for 3 hrs and concentrated in a vacuum. The concentrate was extracted with ethyl acetate and water and the organic layer was dried over anhydrous magnesium sulfate and concentrated in a vacuum. The residue was purified by silica gel column chromatography using a mixture of hexane:ethyl acetate (8:1, v/v) to give the object compound in a syrup form (702.1 mg, 65%).

$^1$H-NMR (CDCl$_3$) δ 6.16 (s, 1H), 4.86 (dd, 1H, J=3.6, 6.0 Hz), 4.66 (d, 1H, J=6.0 Hz), 4.12 (d, 1H, J=6.4 Hz), 3.99 (dd, 1H, J=3.6, 10.8 Hz), 2.05 (s, 3H), 1.48 (s, 3H), 1.33 (s, 3H).

Example 1

Synthesis of (2R,3R,4S)-2-(2-Chloro-6-(3-fluorobenzylamino)-9H-purin-9-yl)tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine A solution of 2,6-dichloropurine (2.29 g, 22.12 mmol) and ammonium sulfate (438 mg, 3.32 mmol) in hexamethyldisilazane (HMDS, 50 ml) was fluxed overnight under inert, dry conditions. The resulting reaction mixture was concentrated in a vacuum and the solid mixture thus formed was re-dissolved in cold 1,2-dichloroethene (20 ml). To this solution were dropwise added a solution of (3aR,4R,6aS)-2,2-dimethyltetrahydrothieno[3,4-d][1,3]dioxol-4-yl acetate (1.41 g, 11.06 mmol), obtained in Preparation Example 1, in 1,2-dichloroethane (20 ml), and then trimethylsilyl trifluoromethanesulfonate (TMSOTf, 4.0 ml, 22.12 mmol). The resulting solution was stirred at 0° C. for 30 min and then at room temperature for 1 hr, and heated at 80° C. for 2 hrs with stirring. The reaction mixture was cooled, diluted in dichloromethane and washed with a saturated aqueous sodium hydrogen carbonate (NaHCO$_3$) solution. The organic solvent was dried over anhydrous magnesium sulfate (MgSO$_4$) and concentrated in a vacuum to give a residue in the form of a yellow syrup. The residue was purified through silica gel column chromatography using a mixture of dichloromethane:methanol (50:1, v/v) as an elution solvent to afford the object compound in the form of a foam (3.03 g, 79%).

UV (CH$_2$Cl$_2$) λ$_{max}$ 275.0 nm;

$^1$H-NMR (CDCl$_3$) δ 8.17 (s, 1H), 5.87 (s, 1H), 5.32 (pseudo t, 1H, J=4.8 Hz), 5.21 (d, 1H, J=5.6 Hz), 3.79 (dd, 1H, J=4.4, 12.8 Hz), 3.26 (d, 1H, J=13.2 Hz), 1.59 (s, 3H), 1.36 (s, 3H);

$[α]^{25}_D$-42.04 (c 0.16, CH$_2$Cl$_2$);

FAB-MS m/z 347 [M+H]$^+$.

Step 2. Preparation of (2R,3S,4S)-2-(2,6-dichloro-9H-purin-9-yl)tetrahydrothiophen-3,4-diol To a solution of 2,6-dichloro-9-((3aR,4R,6aS)-2,2-dimethyltetrahydrothieno[3,4-d][1,3]dioxol-4-yl)-9H-purine, prepared in Step 1, in tetrahydrofuran (20 ml) was added 2 N HCl, followed by stirring the solution overnight. The reaction mixture was neutralized with 1 N sodium hydroxide and carefully concentrated in a vacuum. The concentrate was purified through silica gel column chromatography using a mixture of dichloromethane:methanol (20:1, v/v) as an elution solvent to afford the object compound as a white solid (1.94 g, 96%).

m.p. 198.3-200.3° C.;

UV (MeOH) $\lambda_{max}$ 275 nm;
$^1$H-NMR (CD$_3$OD) δ 8.87 (s, 1H), 6.08 (d, 1H, J=6.8 Hz), 4.69 (q, 1H, J=3.2 Hz), 4.48 (q, 1H, J=3.6 Hz), 3.56 (dd, 1H, J=4.4, 11.2 Hz), 2.97 (dd, 1H, J=3.4, 11.2 Hz);
$[\alpha]^{25}{}_D$-50.43 (c 0.12, DMSO);
FAB-MS m/z 307 [M+H]+.

Step 3. Preparation of (2R,3R,4S)-2-(2-chloro-6-(3-fluorobenzylamino)-9H-purin-9-yl)tetrahydrothiophen-3,4-diol (2R,3S,4S)-2-(2,6-dichloro-9H-purin-9-yl)tetrahydrothiophen-3,4-diol (1 equivalent), prepared in Step 2, and 3-fluorobenzylamine (1.5 equivalents) were dissolved in ethanol (5 ml) at room temperature for 2-3 hrs with stirring. The reaction mixture was concentrated in a vacuum and the concentrate was purified through silica gel column chromatography using a mixture of dichloromethane:methanol (20:1, v/v) as an elution solvent to afford the object compound (0.10 g, 80%).
m.p. 183.2-183.5° C.;
UV (MeOH) $\lambda_{max}$ 275.0 nm;
$^1$H-NMR (DMSO-d$_6$) δ 8.91 (t, 1H—NH, J=5.8 Hz), 8.51 (s, 1H), 7.33-7.39 (m, 1H), 7.13-7.18 (m, 2H), 7.06 (dt, 1H, J=2.8, 11.6 Hz), 5.82 (d, 1H, J=7.2 Hz), 5.56 (d, 1H—OH, J=6.0 Hz), 5.37 (d, 1H—OH, J=4.4 Hz), 4.65 (d, 1H, J=6.0 Hz), 4.60 (m, 1H), 4.33-4.35 (m, 1H), 3.41 (dd, 1H, J=4.0, 10.8 Hz), 2.79 (dd, 1H, J=2.8, 10.8 Hz);
$[\alpha]^{25}{}_D$-96.21 (c 0.12, DMSO);
FAB-MS m/z 396 [M+H]+.

Example 2

Synthesis of (2R,3R,4S)-2-(2-Chloro-6-(3-chlorobenzylamino)-9H-purin-9-yl)tetrahydrothiophen-3,4-diol

Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3 S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of (2R,3R,4S)-2-(2-chloro-6-(3-chlorobenzylamino)-9H-purin-9-yl)tetrahydrothiophen-3,4-diol A procedure similar to that of Step 3 of Example 1 was conducted, with the exception that 3-chlorobenzylamine was used instead of 3-fluorobenzylamine, to give the object compound (0.11 g, 83%).
m.p. 163.3-165.3° C.;
UV (MeOH) $\lambda_{max}$ 274.5 nm;
$^1$H-NMR (CD$_3$OD) δ 8.34 (s, 1H), 7.41 (s, 1H), 7.24-7.34 (m, 3H), 5.94 (d, 1H, J=6.4 Hz), 4.75 (brs, 2H), 4.61 (q, 1H, J=3.2 Hz), 4.45 (q, 1H, J=4.0 Hz), 3.51 (dd, 1H, J=4.8, 11.2 Hz), 2.95 (dd, 1H, J=3.6, 10.8 Hz);
FAB-MS m/z 411 [M]+.

Example 3

Synthesis of (2R,3R,4S)-2-(2-Chloro-6-(3-bromobenzylamino)-9H-purin-9-yl)tetrahydrothiophen-3,4-diol

Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3 S,4S)-2-(2,6-dichloro-9H-purin-9-yl)tetrahydrothiophen-3,4-diol The same procedure as in Step 2 of Example 2 was conducted to give the object compound as a white solid.

Step 3. Preparation of (2R,3R,4S)-2-(2-chloro-6-(3-bromobenzylamino)-9H-purin-9-yl)tetrahydrothiophen-3,4-diol A procedure similar to that of Step 3 of Example 1 was conducted, with the exception that 3-bromobenzylamine was used instead of 3-fluorobenzylamine, to give the object compound (0.12 g, 83%).
m.p. 184.0-185.0° C.;
UV (MeOH) $\lambda_{max}$ 274.0 nm;
$^1$H-NMR (DMSO-d$_6$) δ 8.91 (brs, 1H—NH), 8.51 (s, 1H), 7.55 (s, 1H), 7.43 (d, 1H, J=7.6 Hz), 7.33-7.35 (m, 1H), 7.26-7.30 (m, 1H), 5.82 (d, 1H, J=7.2 Hz), 5.57 (d, 1H—OH, J=6.0 Hz), 5.38 (d, 1H—OH, J=4.0 Hz), 4.60-4.63 (m, 3H), 4.34 (s, 1H), 3.41 (dd, 1H, J=4.4, 11.2 Hz), 2.80 (dd, 1H, J=2.8, 10.8 Hz);
FAB-MS m/z 456 [M+H]+.

Example 4

Synthesis of (2R,3R,4S)-2-(2-Chloro-6-(3-iodobenzylamino)-9H-purin-9-yl)tetrahydrothiophen-3,4-diol

Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3 S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of (2R,3R,4S)-2-(2-chloro-6-(3-iodobenzylamino)-9H-purin-9-yl)tetrahydrothiophen-3,4-diol A procedure similar to that of Step 3 of Example 1 was conducted, with the exception that 3-iodobenzylamine was used instead of 3-fluorobenzylamine, to give the object compound (0.14 g, 84%).
m.p. 198.7-199.9° C.;
UV (MeOH) $\lambda_{max}$ 274.0 nm;

¹H-NMR (DMSO-d₆) δ 8.90 (t, 1H—NH, J=6.4 Hz), 8.51 (s, 1H), 7.74 (s, 1H), 7.60 (d, 1H, J=7.6 Hz), 7.35 (d, 1H, J=7.6 Hz), 7.13 (t, 1H, J=8.0 Hz), 5.82 (d, 1H, J=7.6 Hz), 5.56 (d, 1H, J=6.4 Hz), 5.37 (d, 1H, J=4.0 Hz), 4.60 (d, 3H, J=4.4 Hz), 4.34 (brs, 1H), 3.38 (dd, 1H, J=4.0, 10.8 Hz), 2.80 (dd, 1H, J=4.0, 10.8 Hz);
$[\alpha]^{25}_D$-78.91 (c 0.13, DMSO);
FAB-MS m/z 504 [M+H]+.

Example 5

Synthesis of (2R,3R,4S)-2-(2-Chloro-6-(2-chlorobenzylamino)-9H-purin-9-yl)tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3 S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of (2R,3R,4S)-2-(2-chloro-6-(2-chlorobenzylamino)-9H-purin-9-yl)tetrahydrothiophen-3,4-diol A procedure similar to that of Step 3 of Example 1, with the exception that 2-chlorobenzylamine was used instead of 3-fluorobenzylamine, was conducted to give the object compound (0.11 g, 81%).
m.p. 198.7-199.7° C.;
UV (MeOH) $\lambda_{max}$ 273.5 nm;
¹H-NMR (CD₃OD) δ 8.35 (brs, 1H), 7.45-7.47 (m, 1H), 7.39-7.43 (m, 1H), 7.25-7.29 (m, 2H), 5.95 (d, 1H, J=6.4 Hz), 4.60-4.63 (m, 1H), 4.45 (dd, 1H, J=3.6, 8.0 Hz), 3.51 (dd, 1H, J=4.8, 10.8 Hz), 2.95 (dd, 1H, J=4.0, 10.8 Hz);
$[\alpha]^{25}_D$-96.21 (c 0.12, DMSO);
FAB-MS m/z 412 [M+H]⁺.

Example 6

Synthesis of (2R,3R,4S)-2-(2-Chloro-6-(5-chloro-2-methoxybenzylamino)-9H-purin-9-yl)tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in a foam form.

Step 2. Preparation of (2R,3 S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of (2R,3R,4S)-2-(2-chloro-6-(5-chloro-2-methoxybenzylamino)-9H-purin-9-yl)tetrahydrothiophen-3,4-diol A procedure similar to that of Step 3 of Example 1 was conducted, with the exception that 5-chloro-2-methoxybenzylamine was used instead of 3-fluorobenzylamine, to give the object compound (0.11 g, 78%).
m.p. 188.8-189.8° C.;
UV (MeOH) $\lambda_{max}$ 275.5 nm;
¹H-NMR (DMSO-d₆) δ 8.64 (t, 1H—NH, J=6.0 Hz), 8.51 (s, 1H), 7.21-7.25 (m, 1H), 7.12 (d, 1H, J=7.2 Hz), 7.00 (d, 1H, J=8.0 Hz), 6.85-6.89 (m, 1H), 5.82 (d, 1H, J=7.6 Hz), 5.57 (d, 1H—OH, J=6.4 Hz), 5.37 (d, 1H—OH, J=4.0 Hz), 4.61-4.63 (m, 2H), 4.35 (m, 1H), 3.84 (s, 3H), 3.71 (dd, 1H, J=3.6, 10.4 Hz), 2.80 (dd, 1H, J=2.4, 10.8 Hz);
$[\alpha]^{25}_D$-96.10 (c 0.21, DMSO);
FAB-MS m/z 442 [M+H]+.

Example 7

Preparation of (2R,3R,4S)-2-(2-chloro-6-(2-methoxybenzylamino)-9H-purin-9-yl)tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in a foam form.

Step 2. Preparation of (2R,3 S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of (2R,3R,4S)-2-(2-chloro-6-(2-methoxybenzylamino)-9H-purin-9-yl)tetrahydrothiophen-3,4-diol A procedure similar to that of Step 3 of Example 1 was conducted, with the exception that 2-methoxybenzylamine was used instead of 3-fluorobenzylamine, to give the object compound (0.12 g, 88%).
m.p. 188.0° C.;
UV (MeOH) $\lambda_{max}$ 276.5 nm;
¹H-NMR (DMSO-d₆) δ 8.65 (t, 1H—NH, J=6.0 Hz), 8.51 (s, 1H), 7.21-7.25 (m, 1H), 7.12 (d, 1H, J=7.2 Hz), 7.00 (d, 1H, J=8.0 Hz), 6.85-6.89 (m, 1H), 5.83 (d, 1H, J=6.8 Hz), 5.58 (d, 1H—OH, J=6.4 Hz), 5.39 (d, 1H—OH, J=3.6 Hz), 4.62-4.64 (m, 2H), 4.35 (s, 1H), 3.84 (s, 1H), 3.42 (dd, 1H, J=3.6, 10.4 Hz), 2.79-2.82 (m, 1H);
$[\alpha]^{25}_D$-93.53 (c 0.17, DMSO);
FAB-MS m/z 407 [M+H]+.

Example 8

Synthesis of (2R,3R,4S)-2-(2-Chloro-6-(naphthalen-1-ylmethylamino)-9H-purin-9-yl)tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of (2R,3R,4S)-2-(2-chloro-6-(naphthalen-1-ylmethylamino)-9H-purin-9-yl)tetrahydrothiophen-3,4-diol A procedure similar to that of Step 3 of Example 1 was conducted, with the exception that naphthalen-1-ylmethylamine was used instead of 3-fluorobenzylamine, to give the object compound (0.13 g, 90%).

m.p. 226.3° C. (decomp);

UV (MeOH) $\lambda_{max}$ 281.0 nm;

$^1$H-NMR (DMSO-$d_6$) δ 8.96 (t, 1H—NH, J=6.0 Hz), 8.51 (s, 1H), 8.25 (d, 1H, J=8.0 Hz), 7.95-7.97 (m, 1H), 7.83-7.85 (m, 1H), 7.53-7.61 (m, 2H), 7.43-7.46 (m, 2H), 5.82 (d, 1H, J=7.6 Hz), 5.56 (d, 1H, J=6.4 Hz), 5.38 (d, 1H, J=4.0 Hz), 5.12 (d, 1H, J=6.0 Hz), 4.59-4.61 (m, 1H), 4.34-4.35 (m, 1H), 3.40-3.44 (m, 1H), 2.80 (dd, 1H, J=2.4, 6.8 Hz);

FAB-MS m/z 428 [M+H]+.

Example 9

Synthesis of 3-((2-chloro-9-((2R,3R,4S)-3,4-dihydroxytetrahydrothiophen-2-yl)-9H-purine-6-ylamino)methyl)benzoic acid Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of 3-((2-chloro-9-((2R,3R,4S)-3,4-dihydroxytetrahydrothiophen-2-yl)-9H-purine-6-ylamino)methyl)benzoic acid A procedure similar to that of Step 3 of Example 1 was conducted, with the exception that 3-(aminomethyl)benzoic acid was used instead of 3-fluorobenzylamine, to give the object compound (0.12 g, 84%).

mp 254.0-256.9° C.;

UV (MeOH) $\lambda_{max}$ 275.5 nm;

$^1$H-NMR (DMSO-$d_6$) δ 8.95 (t, 1H—NH, J=6.0 Hz), 8.52 (s, 1H), 7.89 (d, 1H, J=8.4 Hz), 7.43 (d, 1H, J=8.0 Hz), 5.82 (d, 1H, J=7.6 Hz), 5.57 (brs, 1H), 5.38 (brs, 1H), 4.71 (d, 1H, J=6.0 Hz), 4.60 (brs, 1H), 4.34 (brs, 1H), 3.41 (dd, 1H, J=4.0, 10.8 Hz), 2.80 (dd, 1H, J=2.8, 10.8 Hz);

$[\alpha]^2_D$-94.55 (c 0.11, DMSO);

FAB-MS m/z 422 [M+H]$^+$.

Example 10

Synthesis of 2-(2-Chloro-6-methylamino-purin-9-yl)(2R,3S,4R)-tetrahydrothiophen-3,4-diol Step 1. Preparation of 2,6-dichloro-9-((3aR,4R,6aS)-2,2-dimethyltetrahydrothieno[3,4-d][1,3]dioxol-4-yl)-9H-purine The same procedure as in Step 1 of Example 1 was conducted to give the object compound in foam form.

Step 2. Preparation of (2R,3S,4S)-2-(2,6-dichloro-9H-purin-9-yl)tetrahydrothiophen-3,4-diol The same procedure as in Step 2 of Example 1 was conducted to give the object compound as a white solid.

Step 3. Preparation of 2-(2-chloro-6-methylamino-purin-9-yl) (2R,3S,4R)-tetrahydrothiophen-3,4-diol A procedure similar to that of Step 3 of Example 1 was conducted, with the exception that methylamine was used instead of 3-fluorobenzylamine, to give the object compound (0.89 g, 90%).

UV (MeOH) $\lambda_{max}$ 269.5 nm (pH 7);

$^1$H-NMR (CDCl$_3$) δ 2.99 (1H, dd, 4'-CH, J=4.4, 10.8 Hz), 3.12 (3H, brs, NH—CH$_3$), 3.44 1H, dd, 4'-CH, J=4, 10.8 Hz), 4.41 (1H, m, 2'-CH, J=5.6 Hz), 4.47 (1H, m, 3'-CH), 5.89 (1H, d, 1'-CH, J=5.6 Hz), 8.40 (s, 1H, 8-CH);

$[\alpha]^{25}_D$-34.8 (c 0.115, DMSO);

FAB-MS m/z 302.3 [M+H]$^+$.

Example 11

Synthesis of (2R,3R,4S)-2-(6-(3-fluorobenzylamino)-9H-purin-9-yl)tetrahydrothiophen-3,4-diol Step 1. Preparation of 6-chloro-9-((3aR,4R,6aS)-2,2-dimethyltetrahydrothieno[3,4-d][1,3]dioxol-4-yl)-9H-purine A procedure similar to that of Step 1 of Example 1 was conducted, with the exception that 6-chloropurine (2.29 g, 22.12 mmol) was used instead of 2,6-chloropurine, to give the object compound in foam form (1.84 g, 91%).

UV (CH$_2$Cl$_2$) $\lambda_{max}$ 265.0 nm;

$^1$H-NMR (CDCl$_3$) δ 8.67 (pseudo t, 1H, J=1.4 Hz), 8.23 (s, 1H), 5.88 (s, 1H), 5.23 (m, 2H), 3.69 (dd, 1H, J=4.0, 13.2 Hz), 3.18 (d, 1H, J=12.8 Hz), 1.52 (s, 3H), 1.29 (s, 3H);

$^{13}$C-NMR (CDCl$_3$) δ 152.05, 151.39, 151.09, 144.34, 132.56, 111.90, 89.60, 84.31, 70.30, 40.76, 26.40, 24.63;

$[\alpha]^{25}_D$-157.64 (c 0.15, MeOH);

FAB-MS m/z 313 [M+H]+.

Step 2. Preparation of (2R,3S,4S)-2-(6-chloro-9H-purin-9-yl)tetrahydrothiophen-3,4-diol Synthesis was conducted from 6-chloro-9-((3aR,4R,6aS)-2,2-dimethyltetrahydrothieno[3,4-d][1,3]dioxol-4-yl)-9H-purine (1.84 g, 5.88 mmol), prepared in Step 1, in a manner similar to that of Step 2 of Example 1 to afford the object compound as a white solid (1.27 g, 79%).

m.p. 192.3-192.8° C.;

UV (MeOH) A 264.5 nm;

$^1$H-NMR (DMSO-$d_6$) δ 9.02 (s, 1H), 8.82 (s, 1H), 6.02 (d, 1H, J=7.6 Hz), 5.62 (d, 1H—OH, J=6.0 Hz), 5.43 (d,

1H—OH, J=4.0 Hz), 4.70-4.74 (m, 1H), 4.36-4.40 (m, 1H), 3.47 (dd, 1H, J=4.0, 10.8 Hz), 3.17 (d, 1H, J=5.2 Hz), 2.84 (dd, 1H, J=2.8, 11.2 Hz);
$[\alpha]^{25}_D$-109.15 (c 0.16, DMSO);
FAB-MS m/z 273 [M+H]+.

Step 3. Preparation of (2R,3R,4S)-2-(6-(3-fluorobenzylamino)-9H-purin-9-yl)tetrahydrothiophen-3,4-diol (2R,3S,4S)-2-(6-chloro-9H-purin-9-yl)tetrahydrothiophen-3,4-diol (1 equivalent), prepared in Step 2, and 3-fluorobenzylamine (1.5 equivalents) were dissolved in ethanol (5 ml) at room temperature for 2-3 hrs with stirring. The reaction mixture was concentrated in a vacuum and the concentrate was purified through silica gel column chromatography using a mixture of dichloromethane:methanol (20:1, v/v) as an elution solvent to afford the object compound (0.11 g, 82%).
m.p. 180.5-180.7° C.;
UV (MeOH) λ. 273.5 nm;
$^1$H-NMR (DMSO-$d_6$) δ 8.46 (s, 1H), 8.22 (s, 1H), 7.31-7.39 (m, 1H), 7.12-7.18 (m, 2H), 7.01-7.05 (m, 1H), 5.90 (d, 1H, J=7.2 Hz), 5.53 (d, 1H—OH, J=6.4 Hz), 5.35 (d, 1H—OH, J=4.0 Hz), 4.67-4.71 (m, 2H), 4.35-4.37 (m, 1H), 3.39-3.43 (m, 1H), 3.17 (d, 1H, J=5.2 Hz), 2.80 (dd, 1H, J=3.2, 11.2 Hz);
$[\alpha]^{25}_D$-141.2 (c 0.11, DMSO);
FAB-MS m/z 362 [M+H]+.

Example 12

Synthesis of (2R,3R,4S)-2-(6-(3-chlorobenzylamino)-9H-purin-9-yl)tetrahydrothiophen-3,4-diol Step 1. Preparation of 6-chloro-9-((3aR,4R,6aS)-2,2-dimethyltetrahydrothieno[3,4-d][1,3]dioxol-4-yl)-9H-purine The same procedure as in Step 1 of Example 11 was conducted to give the object compound in foam form.

Step 2. Preparation of (2R,3S,4S)-2-(6-chloro-9H-purin-9-yl)tetrahydrothiophen-3,4-diol The same procedure as in Step 2 of Example 11 was conducted to give the object compound as a white solid.

Step 3. Preparation of (2R,3R,4S)-2-(6-(3-chlorobenzylamino)-9H-purin-9-yl)tetrahydrothiophen-3,4-diol A procedure similar to that of Step 3 of Example 11 was conducted, with the exception that 3-chlorobenzylamine was used instead of 3-fluorobenzylamine, to give the object compound (0.12 g, 85%).
m.p. 165.0-165.3° C.;
UV (MeOH) $\lambda_{max}$ 274.5 nm;
$^1$H-NMR (DMSO-$d_6$) δ 8.47 (s, 1H), 8.22 (s, 1H), 7.39 (s, 1H), 7.26-7.35 (m, 3H), 5.91 (d, 1H, J=7.2 Hz), 5.53 (d, 1H—OH, J=6.4 Hz), 5.35 (d, 1H—OH, J=4.0 Hz), 4.67-4.71 (m, 2H), 4.33-4.37 (m, 1H), 3.40-3.48 (m, 2H), 2.80 (dd, 1H, J=3.2, 10.4 Hz);
$[\alpha]^{25}_D$-162.5 (c 0.10, DMSO);
FAB-MS m/z 378 [M+H]+.

Example 13

Synthesis of (2R,3R,4S)-2-(6-(3-bromobenzylamino)-9H-purin-9-yl)tetrahydrothiophen-3,4-diol Step 1. Preparation of 6-chloro-9-((3aR,4R,6aS)-2,2-dimethyltetrahydrothieno[3,4-d][1,3]dioxol-4-yl)-9H-purine The same procedure as in Step 1 of Example 11 was conducted to give the object compound in foam form.

Step 2. Preparation of (2R,3S,4S)-2-(6-chloro-9H-purin-9-yl)tetrahydrothiophen-3,4-diol The same procedure as in Step 2 of Example 11 was conducted to give the object compound as a white solid.

Step 3. Preparation of (2R,3R,4S)-2-(6-(3-bromobenzylamino)-9H-purin-9-yl)tetrahydrothiophen-3,4-diol A procedure similar to that of Step 3 of Example 11 was conducted, with the exception that 3-bromobenzylamine was used instead of 3-fluorobenzylamine, to give the object compound (0.11 g, 70%).
m.p. 183.0-184.0° C.;
UV (MeOH) $\lambda_{max}$ 270.0 nm;
$^1$H-NMR (DMSO-$d_6$) δ 8.46 (s, 1H), 8.22 (s, 1H), 7.53 (s, 1H), 7.39-7.42 (m, 1H), 7.34-7.35 (m, 1H), 7.24-7.28 (m, 1H), 5.90 (d, 1H, J=7.2 Hz), 5.53 (d, 1H—OH, J=6.4 Hz), 5.35 (d, 1H—OH, J=4.0 Hz), 4.67-4.71 (m, 2H), 4.35-4.37 (m, 1H), 3.41 (dd, 1H, J=4.0, 10.8 Hz), 3.06 (q, 1H, J=7.2 Hz), 2.80 (dd, 1H, J=2.8, 10.8 Hz);
$[\alpha]^{25}_D$-100.72 (c 0.14, DMSO);
FAB-MS m/z 422 [M+H]+.

Example 14

Synthesis of (2R,3R,4S)-2-(6-(3-Iodobenzylamino)-9H-purin-9-yl)tetrahydrothiophen-3,4-diol Step 1. Preparation of 6-chloro-9-((3aR,4R,6aS)-2,2-dimethyltetrahydrothieno[3,4-d][1,3]dioxol-4-yl)-9H-purine The same procedure as in Step 1 of Example 11 was conducted to give the object compound in foam form.

Step 2. Preparation of (2R,3S,4S)-2-(6-chloro-9H-purin-9-yl)tetrahydrothiophen-3,4-diol The same procedure as in Step 2 of Example 11 was conducted to give the object compound as a white solid.

Step 3. Preparation of (2R,3R,4S)-2-(6-(3-iodobenzylamino)-9H-purin-9-yl)tetrahydrothiophen-3,4-diol A procedure similar to that of Step 3 of Example 11 was conducted, with the exception that 3-iodobenzylamine was used instead of 3-fluorobenzylamine, to give the object compound (0.12 g, 72%).
m.p. 198.8-199.8° C.;
UV (MeOH) $\lambda_{max}$ 271.5 nm;
$^1$H-NMR (DMSO-$d_6$) δ 8.46 (s, 1H), 8.22 (s, 1H), 7.72 (s, 1H), 7.56-7.59 (m, 1H), 7.35-7.36 (d, 1H, J=7.6 Hz), 7.01-

7.12 (m, 1H), 5.90 (d, 1H, J=7.2 Hz), 5.53 (d, 1H—OH, J=6.4 Hz), 5.35 (d, 1H—OH, J=4.4 Hz), 4.67-4.71 (m, 2H), 4.34-4.38 (m, 1H), 3.41 (dd, 1H, J=4.0, 10.8 Hz), 3.16 (d, 1H, J=7.2 Hz), 2.80 (dd, 1H, J=2.8, 10.8 Hz);
$[\alpha]^{25}{}_D$-97.08 (c 0.14, DMSO);
FAB-MS m/z 470 [M+H]+.

Example 15

Synthesis of (2R,3R,4R)-2-(6-(3-bromobenzylamino)-2-chloro-9H-purin-9-yl)tetrahydrofuran-3,4-diol Step 1. Preparation of 2,6-dichloro-9-((3aR,4R,6aR)-2,2-dimethyltetrahydrofuro[3,4-d][1,3]dioxol-4-yl)-9H-purine Synthesis was conducted using (3aR,4R,6aR)-2,2-dimethyltetrahydrofuro[3,4-d][1,3]dioxol-4-ol (702.1 g, 3.472 mmol), prepared in Preparation Example 2, in the same manner as in Step 1 of Example 1 to afford the object compound in foam form (793.0 mg, 69%).
UV (MeOH) $\lambda_{max}$ 276.5 nm;
$^1$H-NMR (CDCl$_3$) δ 8.15 (s, 1H), 6.07 (s, 1H), 5.41 (d, 1H, J=6.0 Hz), 5.26-5.29 (m, 1H), 4.25-4.31 (m, 2H), 1.57 (s, 3H), 1.41 (s, 3H);
$[\alpha]^{25}{}_D$-21.00 (c 0.10, DMSO);
FAB-MS m/z 331 [M+H]+.

Step 2. Preparation of (2R,3R,4R)-2-(2,6-dichloro-9H-purin-9-yl)tetrahydrofuro-3,4-diol Synthesis was conducted using 2,6-dichloro-9-((3aR,4R,6aS)-2,2-dimethyltetrahydrofuro[3,4-d][1,3]dioxol-4-yl)-9H-purine (900 mg, 2.0 mmol), prepared in Step 1, in the same manner as in Step 2 of Example 1 to give the object compound as a white solid (0.46 g, 80%).
m.p. 122.7-123.4° C.;
UV (MeOH) $\lambda_{max}$ 276.5 nm;
$^1$H-NMR (DMSO-d$_6$) δ 8.98 (s, 1H), 5.96 (d, 1H, J=6.4 Hz), 5.57 (d, 1H—OH, J=6.0 Hz), 5.32 (d, 1H—OH, J=4.0 Hz), 4.69-4.74 (m, 1H), 4.41 (dd, 1H, J=3.6, 9.2 Hz), 4.29-4.32 (m, 1H), 3.87 (dd, 1H, J=2.0, 9.6 Hz);
$[\alpha]^{25}{}_D$-68.09 (c 0.14, DMSO);
FAB-MS m/z 291 [M+H]+.

Step 3. Preparation of (2R,3R,4R)-2-(6-(3-bromobenzylamino)-2-chloro-9H-purin-9-yl)tetrahydrofuro-3,4-diol (2R,3S,4S)-2-(2,6-dichloro-9H-purin-9-yl)tetrahydrofuro-3,4-diol (1 equivalent), prepared in Step 2, and 3-bromobenzylamine (1.5 equivalents) were dissolved in ethanol (5 ml) at room temperature for 2-3 hrs with stirring. The reaction mixture was concentrated in a vacuum and the concentrate was purified through silica gel column chromatography using a mixture of dichloromethane:methanol (20:1, v/v) as an elution solvent to afford the object compound (0.12 g, 82%).
m.p. 181.5-181.7° C.;
UV (MeOH) $\lambda_{max}$ 274.5 nm;
$^1$H-NMR (DMSO-d$_6$) δ 8.92 (t, 1H—NH, J=6.0 Hz), 8.43 (S, 1H), 7.55 (s, 1H), 7.44 (d, 1H, J=8.0 Hz), 7.33-7.35 (m, 1H), 7.26-7.30 (m, 1H), 5.81 (d, 1H, J=6.4 Hz), 5.47 (d, 1H, J=6.4 Hz), 5.22 (d, 1H, J=4.0 Hz), 4.66-4.69 (m, 1H), 4.62 (s, 2H), 4.32 (dd, 1H, J=3.6, 9.2 Hz), 4.25 (brs, 1H), 3.80 (dd, 1H, J=1.6, 9.2 Hz);
$[\alpha]^{25}{}_D$-62.75 (c 0.10, DMSO);
FAB-MS m/z 440 [M+H]+.

Example 16

Synthesis of (2R,3R,4R)-2-(6-(3-iodobenzylamino)-2-chloro-9H-purin-9-yl)tetrahydrofuro-3,4-diol Step 1. Preparation of 2,6-dichloro-9-((3aR,4R,6aR)-2,2-dimethyltetrahydrofuro[3,4-d][1,3]dioxol-4-yl)-9H-purine The same procedure as in Step 1 of Example 15 was conducted to give the object compound in foam form.

Step 2. Preparation of (2R,3R,4R)-2-(2,6-dichloro-9H-purin-9-yl)tetrahydrofuro-3,4-diol The same procedure as in Step 2 of Example 15 was conducted to give the object compound as a white solid in syrup form.

Step 3. Preparation of (2R,3R,4R)-2-(6-(3-iodobenzylamino)-2-chloro-9H-purin-9-yl)tetrahydrofuro-3,4-diol A procedure similar to that of Step 3 of Example 15 was conducted, with the exception that 3-iodobenzylamine was used instead of 3-bromobenzylamine to give the object compound (0.13 g, 78%).
m.p. 195.5-195.8° C.;
UV (MeOH) $\lambda_{max}$ 274.0 nm;
$^1$H-NMR (DMSO-d$_6$) δ 8.91 (t, 1H—NH, J=6.4 Hz), 8.44 (s, 1H), 7.75 (s, 1H), 7.61 (d, 1H, J=8.0 Hz), 7.36 (d, 1H, J=7.6 Hz), 7.13 (t, 1H, J=4.0 Hz), 5.81 (d, 1H, J=6.8 Hz), 5.47 (d, 1H—OH, J=6.8 Hz), 5.23 (d, 1H—OH, J=4.0 Hz), 4.72 (dd, 1H, J=6.4, 10.8 Hz), 4.61 (d, 1H, J=6.0 Hz), 4.34 (dd, 1H, J=3.6, 9.2 Hz), 3.81 (dd, 1H, J=1.2, 9.2 Hz);
$[\alpha]^{25}{}_D$-68.07 (c 0.12, DMSO);
FAB-MS m/z 488 [M+H]$^+$.

Experimental Example 1

Assay for Binding Affinity for Adenosine Receptors
The adenosine derivatives of the present invention were assayed for binding affinity and selectivity for $A_1$, $A_{2A}$ and $A_3$ receptors among human adenosine receptor (hAR) as follows.
CHO cells (ATCC No. CCL-61), in which $A_1$ and $A_3$ adenosine receptors were expressed, were cultured in F-12 media (Gibco, U.S.A.) supplemented with 10% fetal bovine serum (FBS) and penicillin/streptomycin (100 units/ml and 100 g/ml), at 37° C. in a 5% CO$_2$ atmosphere. A predetermined amount of suitable hAR-expressed CHO cells was mixed with labeled ligands (1 nM [$^3$H]CCPA and 0.5 nM [$^{125}$I]AB-MECA) specifically binding to $A_1$ and $A_3$ adenosine receptors in a 50/10/1 buffer in test tubes. The derivatives of the present invention were dissolved at various concentrations in dimethyl sulfoxide (DMSO) and diluted in the buffer, taking care that the final concentration of DMSO did not exceed 1%. Incubation for 1 hr in a 37° C. incubator was followed by rapid filtration in a vacuum using a cell collector (TOMTEC, U.S.A.). Subsequently, the test tubes were washed three times with 3 ml of the buffer before radioactivity was measured using a γ-counter. In the same condition as that for total binding, the equilibrium constant $K_i$ for non-specific binding was determined in the presence of 10

µM of 5'-N-ethylcarboxamidoadenosine (NECA) as a non-labeled ligand. The equilibrium constant $K_i$ was calculated according to the Cheng-Prusoff equation on the assumption that [$^{125}$I]AB-MECA has a $K_d$ value of 1.48 nM. $K_i$ for binding affinity was determined by subtracting the non-specific binding value from the total binding value. On the basis of the specific binding values, the samples were analyzed for binding affinity to various adenosine receptors.

In addition, the binding of the labeled ligand [$^3$H]CGS-21680 (2-(((4-(2-carboxyethyl)phenyl)ethylamino)-5'-N-ethylcarbamoyl)adenosine) to the $A_{2A}$ adenosine receptor expressed on HEK 293 cell (human embryonic kidney cell grown in tissue culture) was assayed as follows. Adenosine deaminase was added alone or in combination with a radio-active ligand when cerebral meninges were incubated at 30° C. for 30 min. Each of the compounds synthesized in the examples was measured for $IC_{50}$ at least 6 different concentrations, and the measurements were analyzed using Sigma-Plot software to determine $K_i$ values. Chemical Structures of the compounds synthesized in the examples, substituents, and $K_i$ values for binding affinity are summarized in Table 1, below.

TABLE 1

| Ex. No. | Structures | Substituents | | | $K_i$ (nM) of % | | |
|---|---|---|---|---|---|---|---|
| | | A | R | Y | $hA_1$ | $hA_{2A}$ | $hA_3$ |
| 1 | | S | 3-fluorobenzyl | Cl | 19.8% | 47.6% | 7.4 ± 1.3 |
| 2 | | S | 3-chlorobenzyl | Cl | 37.9% | 17.7% | 1.66 ± 0.90 |
| 3 | | S | 3-bromobenzyl | Cl | 34.2% | 18.4% | 8.99 ± 5.17 |

TABLE 1-continued

| Ex. No. | Stuctures | Substituents | | | $K_i$ (nM) of % | | |
|---|---|---|---|---|---|---|---|
| | | A | R | Y | $hA_1$ | $hA_{2A}$ | $hA_3$ |
| 4 | | S | 3-iodobenzyl | Cl | 2490 ± 940 | 341 ± 75 | 4.16 ± 0.50 |
| 5 | | S | 2-chlorobenzyl | Cl | 12.8% | 1600 ± 135 | 25.8 ± 6.3 |
| 6 | | S | 5-chloro-2-methoxybenzyl | Cl | 23.8% | 4020 ± 1750 | 12.7 ± 3.7 |
| 7 | | S | 2-methoxybenzyl | Cl | 9.4% | 17.5% | 19.9 ± 7.1 |

TABLE 1-continued

| Ex. No. | Stuctures | Substituents | | | $K_i$ (nM) of % | | |
|---|---|---|---|---|---|---|---|
| | | A | R | Y | $hA_1$ | $hA_{2A}$ | $hA_3$ |
| 8 | | S | 1-naphthylmethyl | Cl | 22.0% | −8.3% | 24.8 ± 8.1 |
| 9 | | S | 3-toluic acid | Cl | 13.1% | −0.18% | 41.5% |
| 10 | | S | methyl | Cl | 55.4 ± 1.8% | 45.0 ± 1.4% | 3.69 ± 0.25 |
| 11 | | S | 3-fluorobenzyl | H | 1430 ± 420 | 1260 ± 330 | 7.3 ± 0.6 |

TABLE 1-continued

| Ex. No. | Stuctures | Substituents | | | $K_1$ (nM) of % | | |
|---|---|---|---|---|---|---|---|
| | | A | R | Y | $hA_1$ | $hA_{2A}$ | $hA_3$ |
| 12 | | S | 3-chlorobenzyl | H | 860 ± 210 | 440 ± 110 | 1.5 ± 0.4 |
| 13 | | S | 3-bromobenzyl | H | 790 ± 190 | 420 ± 32 | 6.8 ± 3.4 |
| 14 | | S | 3-iodobenzyl | H | 530 ± 97 | 230 ± 65 | 2.5 ± 1.0 |
| 15 | | O | 3-bromobenzyl | Cl | 39.8% | 22.8% | 13.0 ± 6.9 |

TABLE 1-continued

| Ex. No. | Stuctures | Substituents | | | $K_i$ (nM) of % | | |
|---|---|---|---|---|---|---|---|
| | | A | R | Y | $hA_1$ | $hA_{2A}$ | $hA_3$ |
| 16 | (structure) | O | 3-iodobenzyl | Cl | 37.7% | 28.6% | 42.9 ± 8.9 |

Unit nM ± SEM
"%" represents percentage inhibition of specific binding of 10 μM labeled ligand in the presence of 10 μM of the unlabeled ligand NECA.

As can be understood from the data of Table 1, the compounds synthesized in the examples of the present invention were found to have high binding affinity for human $A_3$ adenosine receptors ($hA_3AR$), but low affinity for $A_1$ and $A_{2A}$ adenosine receptors, thereby showing high selectivity. Particularly, the compound of Example 12 shows the highest binding affinity for $hA_3$ AR, with $K_i$ determined to be 1.50±0.40 nM, followed by the compound of Example 2 ($K_i$=1.66±0.90 nM), the compound of Example 14 ($K_i$=2.50±1.00 nM), the compound of Example 10 ($K_i$=3.69±0.25 nM) and the compound of Example 4 ($K_i$=4.16±0.50 nM) in decreasing order of binding affinity. Also, the compound of Example 4 was measured to have high binding affinity for the rat $A_3$ adenosine receptor expressed in CHO cells ($K_i$=3.89±1.15 nM) and was not observed as an agonist or antagonist on human $A_{2B}$ adenosine receptor.

In addition, the compounds having halobenzoyl substituents were found to have binding affinity in decreasing order of Cl>I>F>Br. The compound of Example 2, having 3-chlorobenzyl, had higher binding affinity for $hA_3$ adenosine receptor than the compound of Example 5, having 2-chlorobenzyl ($K_i$=25.8±6.3 nM). In addition, the adenosine derivatives having a substituent at the 3-position of the benzene ring in accordance with the present invention had stronger binding affinity for $hA_3AR$ than the adenosine derivatives, having a substituent at the 2- or 4-position, or two substituents at the 2- and 5-position. The compounds of Examples 15 and 16, both adenosine derivatives having 4'-O oxonucleoside forms, also had high binding affinity and selectivity, which were, however, not superior to those of the corresponding 4'-S thionucleoside forms, such as those of Examples 3 and 4. The compounds of Examples 10 to 14, in which the chloro group at the 2-position of the purine base was substituted with a hydrogen atom, were observed to exceed the 2-chloro compounds with regard to binding affinity and selectivity.

Experimental Example 2

Antagonist Effect of Adenosine Derivatives on $A_3$ Adenosine Receptors and cAMP Inhibition In order to examine whether the derivatives of the present invention are effective as human $A_3$ adenosine receptor antagonists, an assay for antagonism and cAMP inhibition was conducted by treating CHO cells with the compound of Example 4 and Cl-IB-MECA.

When CHO cells, in which human $A_3$ adenosine receptor was expressed, were treated with various concentrations of the compound of Example 4, as seen in FIG. 1, the agonist effect of the 100% pure agonist Cl-IB-MECA was observed to be inhibited in a dose-dependent manner, indicating that the compound of the present invention competes with Cl-IB-MECA for the same receptor binding site. Results of a test for human $A_3$ adenosine receptor-mediated cAMP inhibition in the CHO cells demonstrates that the compounds synthesized in the examples of the present invention are 100% pure $A_3$ adenosine receptor antagonists. Thus, the compounds synthesized according to the present invention are found to exhibit a dissociation constant $K_B$ of 1.92 nM, as measured using Schild analysis.

Experimental Examples 3 to 6

Anti-Inflammatory Activity of Adenosine Derivatives

The adenosine derivatives of the present invention were examined for anti-inflammatory activity in the following animal test. Seven-week-old male ICR mice were treated with TPA (12-O-tetradecanoylphorbol-13-acetate, 20 μl) in the right ear. Within 15 minutes, the compounds of Examples 1 to 16 were diluted at a concentration of 0.5% in acetone (20 μl), distilled water, or mixtures of DMSO and acetone (compositions shown in Tables 2 to 5) before being administered to the mice. Hydrocortisone was used at the same concentration as a control.

6 hrs after treatment with TPA, the mice were secondarily treated with the adenosine derivatives of the present invention. 24 hrs after TPA treatment, test animals were euthanized using a cervical dislocation method. Samples were obtained from the right ear using a 6 mm diameter punch. The activity was observed by measuring the ear sample using a microbalance. Percentages of inhibition were calculated using the following Equation 1. The compositions and amounts used in these experiments are summarized in Tables 2 to 5 and the anti-inflammatory activities thereof are shown in FIGS. 2 to 5.

$$\% \text{ Inhibition} = \frac{1 - Rt.\text{Ear(Test-Non treated)}}{Rt.\text{Ear}(TPA \text{ only-Non treated})} \quad \text{[Equation 1]}$$

TABLE 2

| Exp. Ex. 3 | Compositions | Amounts |
|---|---|---|
| 3-1 | Non-treated | — |
| 3-2 | TPA alone | 20 μl |
| 3-3 | TPA + acetone | 20 μl + 20 μl |
| 3-4 | TPA + acetone + Cpd. Of Ex. 2 | 20 μl + 0.5%/20 μl |
| 3-5 | TPA + acetone + Cpd. Of Ex. 3 | 20 μl + 0.5%/20 μl |
| 3-6 | TPA + acetone + Cpd. Of Ex. 4 | 20 μl + 0.5%/20 μl |
| 3-7 | TPA + acetone + hydrocortisone | 20 μl + 0.5%/20 μl |

TABLE 3

| Exp. Ex. 4 | Compositions | Amounts |
|---|---|---|
| 4-1 | Non-treated | — |
| 4-2 | TPA alone | 20 μl |
| 4-3 | TPA + acetone | 20 μl + 20 μl |
| 4-4 | TPA + acetone + Cpd. Of Ex. 1 | 20 μl + 0.5%/20 μl |
| 4-5 | TPA + acetone + Cpd. Of Ex. 6 | 20 μl + 0.5%/20 μl |
| 4-6 | TPA + acetone + hydrocortisone | 20 μl + 0.5%/20 μl |

TABLE 4

| Exp. Ex. 5 | Compositions | Amounts |
|---|---|---|
| 5-1 | Non-treated | — |
| 5-2 | TPA alone | 20 μl |
| 5-3 | TPA + solvent mix (water:acetone 1:4) | 20 μl + 20 μl |
| 5-4 | TPA + solvent mix + Cpd. Of Ex. 5 | 20 μl + 0.5%/20 μl |
| 5-5 | TPA + solvent mix + Cpd. Of Ex. 7 | 20 μl + 0.5%/20 μl |
| 5-6 | TPA + solvent mix + Cpd. Of Ex. 8 | 20 μl + 0.5%/20 μl |
| 5-7 | TPA + solvent mix + hydrocortisone | 20 μl + 0.5%/20 μl |

TABLE 5

| Exp. Ex. 6 | Compositions | Amounts |
|---|---|---|
| 6-1 | Non-treated | — |
| 6-2 | TPA alone | 20 μl |
| 6-3 | TPA + solvent mix (DMSO:acetone 1:9) | 20 μl + 20 μl |
| 6-4 | TPA + solvent mix + Cpd. Of Ex. 15 | 20 μl + 0.5%/20 μl |
| 6-5 | TPA + solvent mix + Cpd. Of Ex. 16 | 20 μl + 0.5%/20 μl |
| 6-6 | TPA + solvent mix + hydrocortisone | 20 μl + 0.5%/20 μl |

When applied to the mice, as seen in FIG. 2, dilutions of the compounds of Examples 2 to 4 were found to inhibit the TPA-induced inflammation of the mouse ear to some degree, although this anti-inflammatory activity was very small compared to that of the control hydrocortisone.

Figure 3:
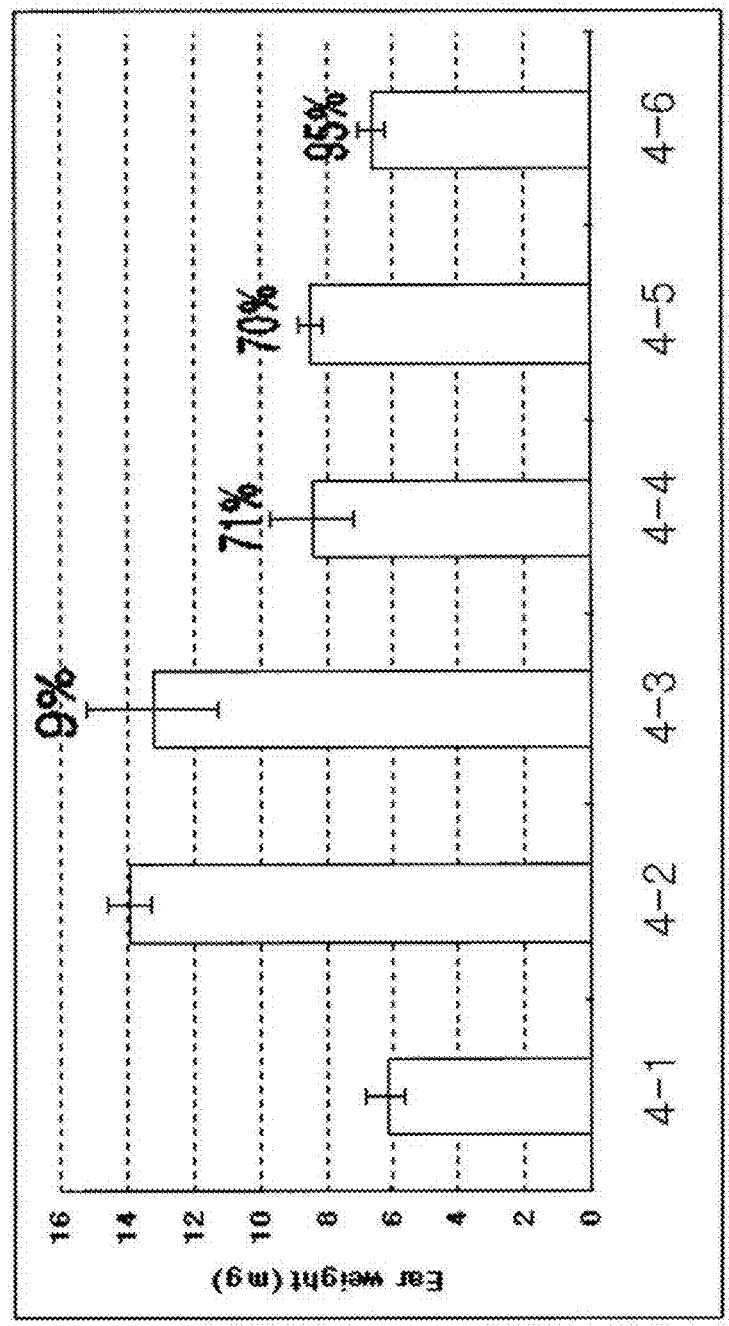
FIG. 3 is a graph showing the anti-inflammatory activity of the compounds (Examples 1 and 6) of the present invention in animal tests.

The anti-inflammatory activity of the compounds of Examples 1 and 6, as shown in FIG. 3, was measured to be four or more times that of the compounds of Examples 2 to 4.

As seen in FIG. 4, the compounds of Examples 5, 7 and 8, diluted at a concentration of 0.5% in a mixture of distilled water and acetone (1:4), were measured to have percentages of inflammation inhibition of 17%, 34% and 53%, respectively.

Figure 5:
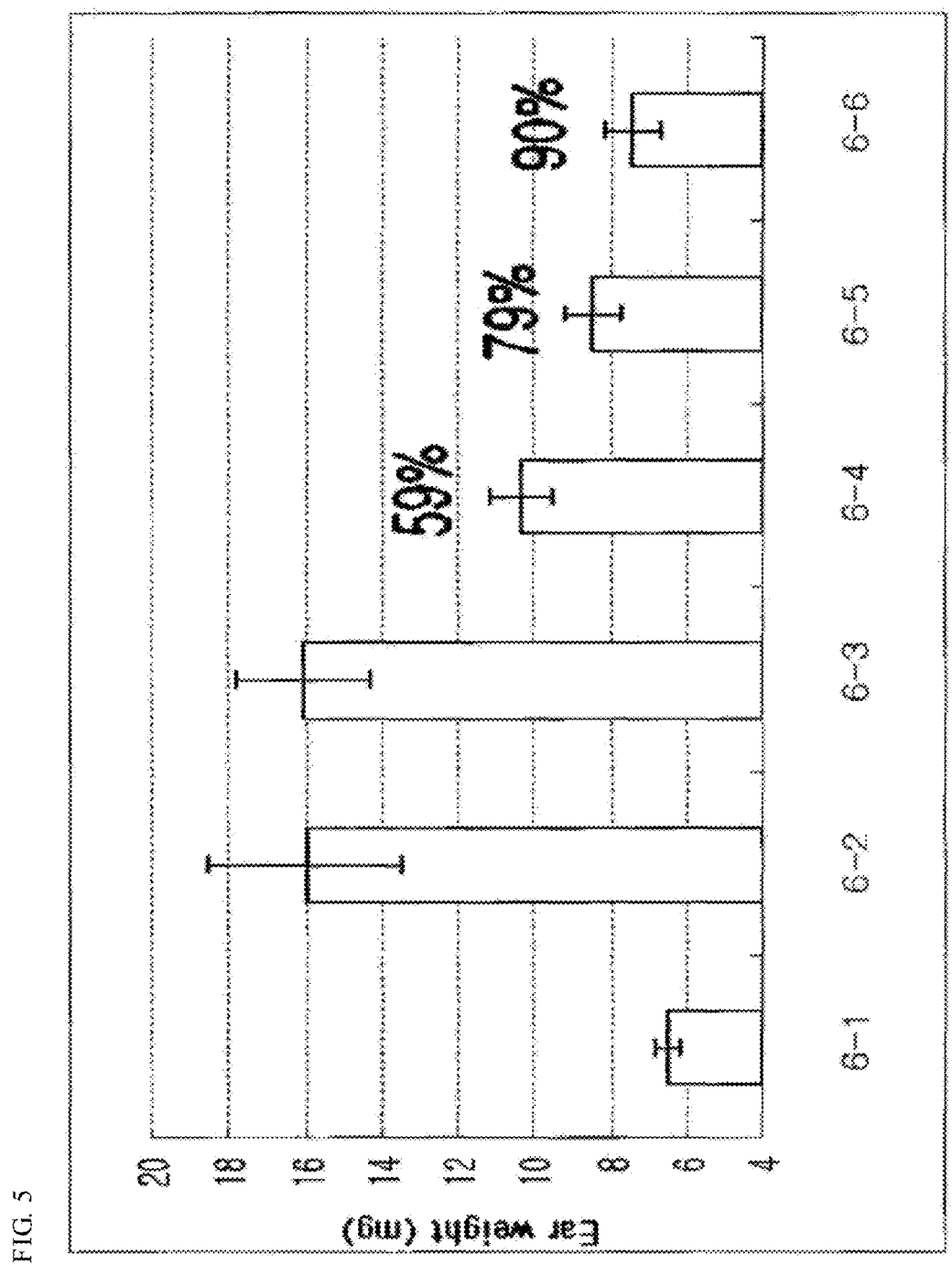
FIG. 5 is a graph showing the anti-inflammatory activity of the compounds (Examples 15 and 16) of the present invention in animal tests.

As shown in FIG. 5, the compounds of Examples 15 and 16, diluted at a concentration of 0.5% in a mixture of DMSO and acetone (1:9), were measured to have percentages of inflammation inhibition of 59% and 79%, respectively. Based on the observations in this test, the adenosine derivatives of the present invention were proven to have anti-inflammatory activity.

Experimental Example 8

Toxicity Assay

The compounds synthesized in the examples of the present invention were assayed for cytotoxicity in animals. Three test groups of three 25±5 g ICR mice (Central Lab. Animal Inc., Korea) and three test groups of three 235±10 g specific pathogen-free (SPF) Sprague Dawley rats (Central Lab Animal Inc., Korea) were intraperitoneal injection with the compound of Example 2 at doses of 20 mg/kg, 10 mg/kg, and 1 mg/kg, respectively, followed by observation for 24 hrs.

No death was observed in all three groups. No difference in weight gain or feed intake was detected between the control group and the test groups. Therefore, the derivative compounds of the present invention were proven as being safe.

The adenosine compounds of the present invention may be administered in the following dosage forms and the following Formulation Examples are set forth to illustrate, but not limit, the present invention.

| <FORMULATION EXAMPLE 1> Preparation of Powder | |
|---|---|
| Adenosine Derivative | 500 mg |
| Corn Starch | 100 mg |
| Lactose | 100 mg |
| Talc | 10 mg |

The ingredients were mixed and filled in an airtight bag.

| <FORMULATION EXAMPLE 2> Preparation of Tablet | |
|---|---|
| Adenosine Derivative | 100 mg |
| Corn Starch | 100 mg |
| Lactose | 100 mg |
| Mg Stearate | 2 mg |

The ingredients were mixed and compressed into tablets according to a conventional method.

| <FORMULATION EXAMPLE 3> Preparation of Capsule | |
|---|---|
| Adenosine Derivative | 50 mg |
| Lactose | 50 mg |
| Mg Stearate | 1 mg |

The ingredients were mixed and filled in gelatin capsules according to a conventional method.

| <FORMULATION EXAMPLE 4> Preparation of Injection | |
|---|---|
| Adenosine Derivative | 10 mg |
| Sterile Water for injection | suitable amount |
| pH Adjuster | Suitable amount |

The pH of a solution of the active ingredient in distilled water was adjusted to 7.5 and the solution was diluted in sterile water to a volume 2 ml and loaded into ampules before sterilization.

<FORMULATION EXAMPLE 5> Preparation of Liquid Form

| | |
|---|---|
| Adenosine Derivative | 1 g |
| Isomerized Sugar | 10 g |
| Sucrose | 10 g |
| Lemon Flavor | suitable amount |
| Pure water | suitable amount |

A liquid dosage form was prepared by dissolving the ingredients in pure water, adding a suitable amount of lemon flavor, increasing the volume to 100 ml with pure water, loading the volume into a brown vial, and sterilizing.

<Formulation Example 6> Preparation of Oral Agent

A suitable amount of the adenosine derivative compound of the inventive concept was used.

A suitable amount of 0.5 wt % methyl cellulose (MC) was used.

An oral agent was prepared by suspending the adenosine derivative compound of the inventive concept in 0.5 wt % methyl cellulose (Wako Pure Chemical Industry, Japan).

<Experimental Example 9> Efficacy Test of the Adenosine Derivative of the Inventive Concept on NASH or NAFLD, Liver Fibrosis and Liver Cirrhosis Animal tests were conducted as follows in order to confirm the efficacy of the adenosine derivative of the inventive concept on NASH or NAFLD and liver fibrosis.

As shown in Table 6, the compound of Example 2 was orally administered to twenty-four NASH- or NAFLD-induced mice (eight in each experimental example below) once a day for six to 10 weeks of age, together with a vehicle (0.5% methyl cellulose).

TABLE 6

| Experimental Example 9 | Dosage |
|---|---|
| 9-1 | 7 mg/kg of the compound of Example 2 + 0.5% MC |
| 9-2 | 15 mg/kg of the compound of Example 2 + 0.5% MC |
| 9-3 | 30 mg/kg of the compound of Example 2 + 0.5% MC |

As a comparison group, eight normal mice were given no treatment until 10 weeks of age. As a positive control group, eight NASH- or NAFLD-induced mice were orally administered with 10 mg/kg of telmisartan (i.e., a hypertension medication) once a day for six to 10 weeks of age. As a negative control group, eight NASH- or NAFLD-induced mice were orally administered with only 10 mL/kg of 0.5% methyl cellulose (i.e., a vehicle) once a day for 6 to 10 weeks of age.

Then, for the livers of the experimental animals at 10 weeks of age, the degree of steatosis, inflammation and ballooning were measured using HE staining, and the area of fibrosis was observed and measured using Sirius red staining. The results were scored by the Bonferroni multiple comparison test and are shown in FIGS. 6 through 11.

In FIGS. 6 through 11, low, medium, and high dose groups represent Experimental Examples 9-1, 9-2, and 9-3, respectively, and normal, vehicle, and telmisartan represent the comparison group, the negative control group, and the positive control group, respectively.

Figure 6:
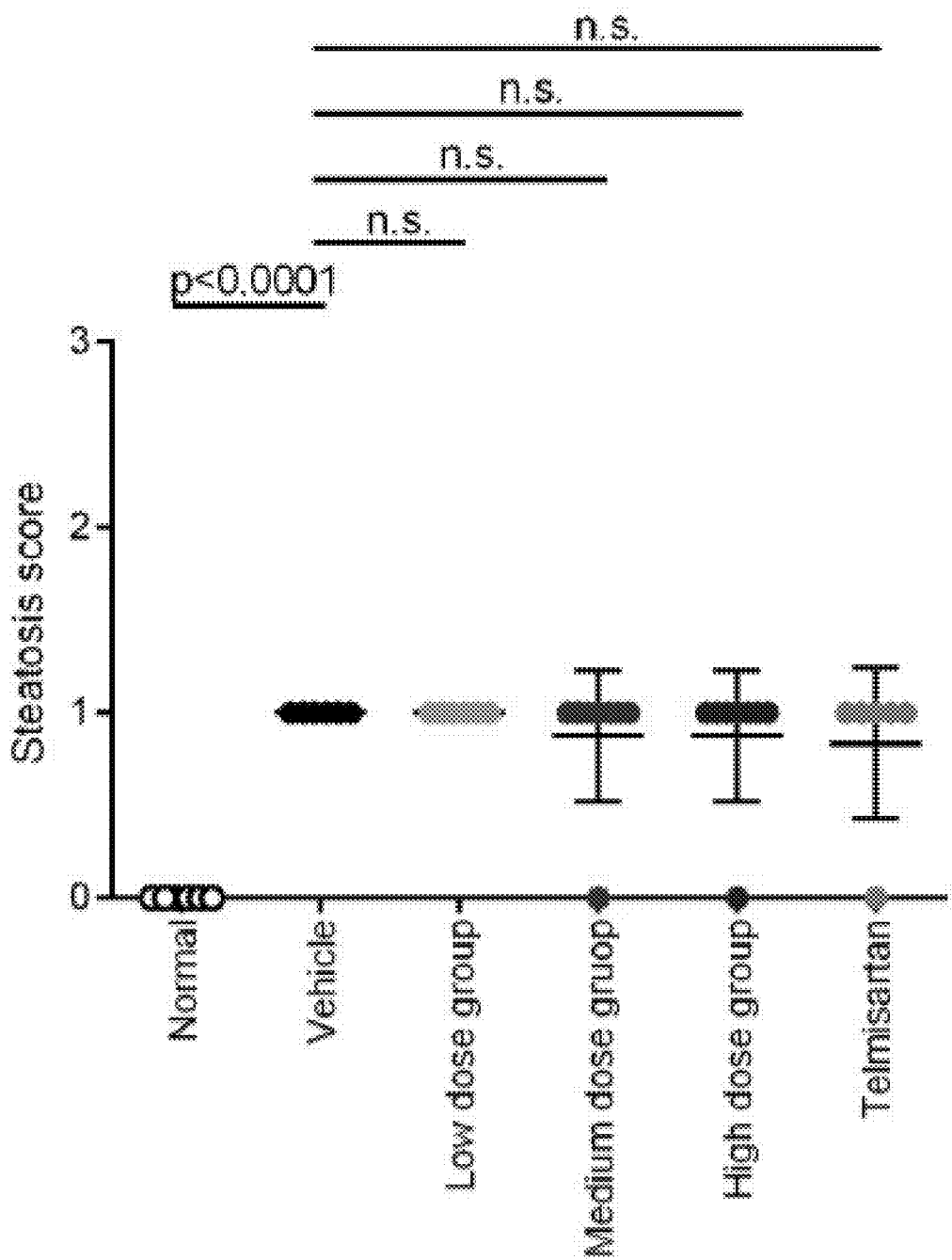
FIG. 6 is a graph showing the steatosis scores of the livers of experimental animals in Experimental Example 9.

FIG. 6 is a graph showing the steatosis scores of the livers of the experimental animals. Referring to FIG. 6, no significant decrease in steatosis was observed in the mice of Experimental Example 9 administered with the adenosine derivative of the inventive concept and in the mice of the positive control group, as compared with the mice of the negative control group.

Figure 7:
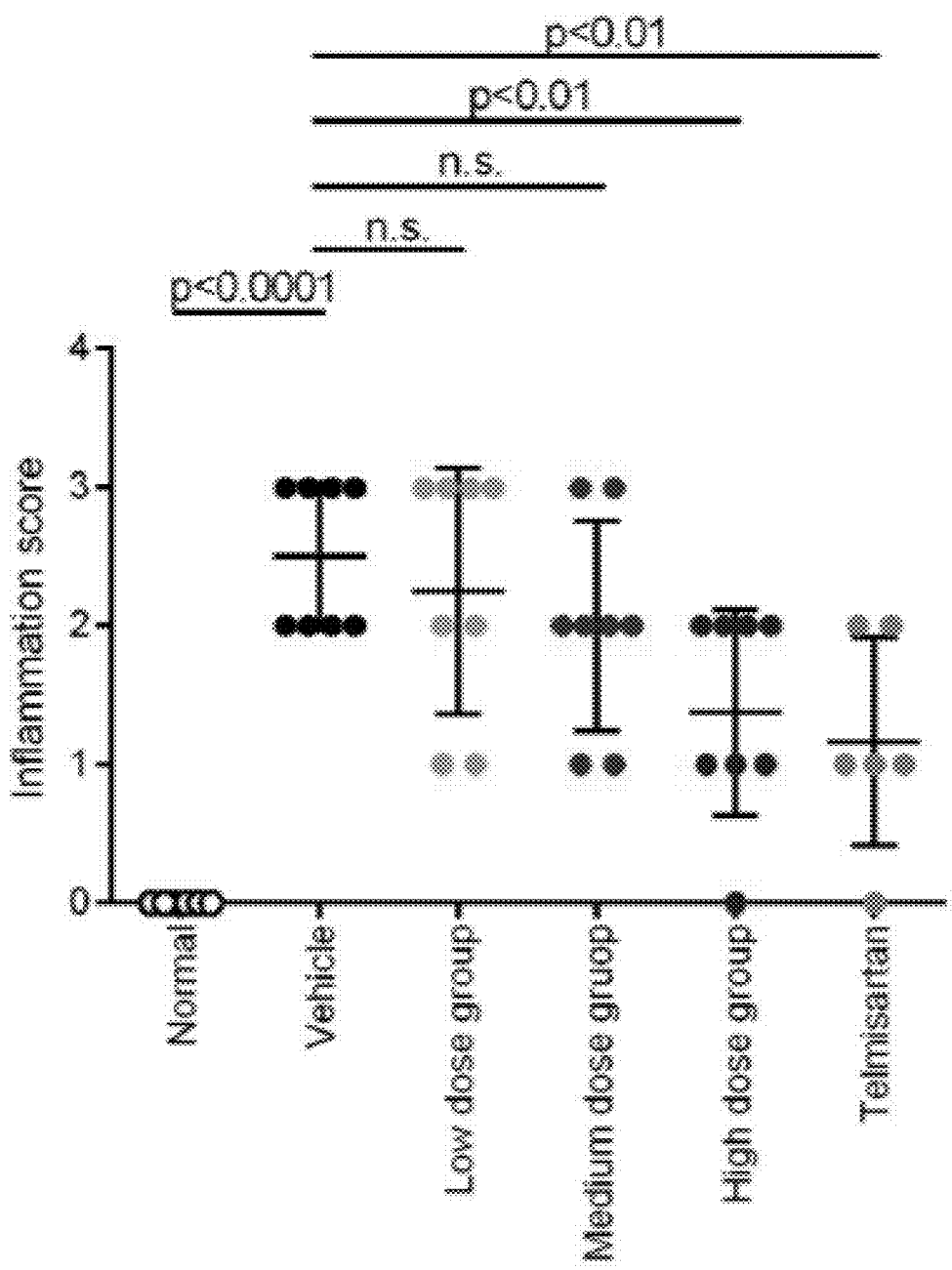
FIG. 7 is a graph showing the inflammation scores of the livers of the experimental animals in Experimental Example 9.

FIG. 7 is a graph showing the inflammation scores of the livers of the experimental animals. Referring to FIG. 7, the mice administered with the adenosine derivative of the inventive concept were found to have anti-inflammatory activity dependent on the dose of the derivative.

Figure 8:
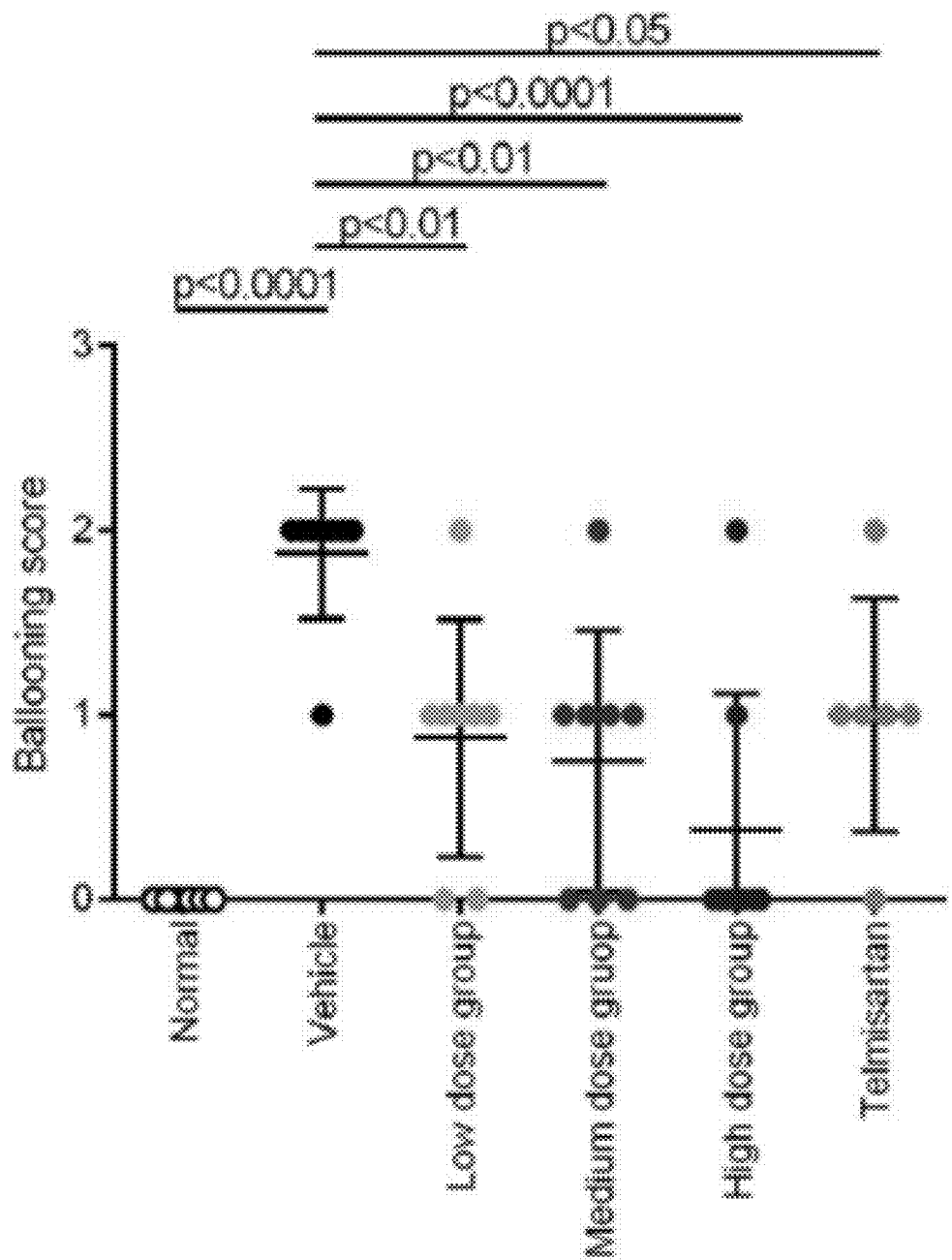
FIG. 8 is a graph showing the ballooning scores of the livers of the experimental animals in Experimental Example 9.

FIG. 8 is a graph showing the ballooning scores of the livers of the experimental animals. Referring to FIG. 8, a derivative dose-dependent reduction in ballooning was observed in the mice administered with the adenosine derivative of the inventive concept. In addition, a noticeable reduction in ballooning was observed in the mice of Experimental Example 9-1 administered with the adenosine derivative of the inventive concept at a low dose.

Figure 9:
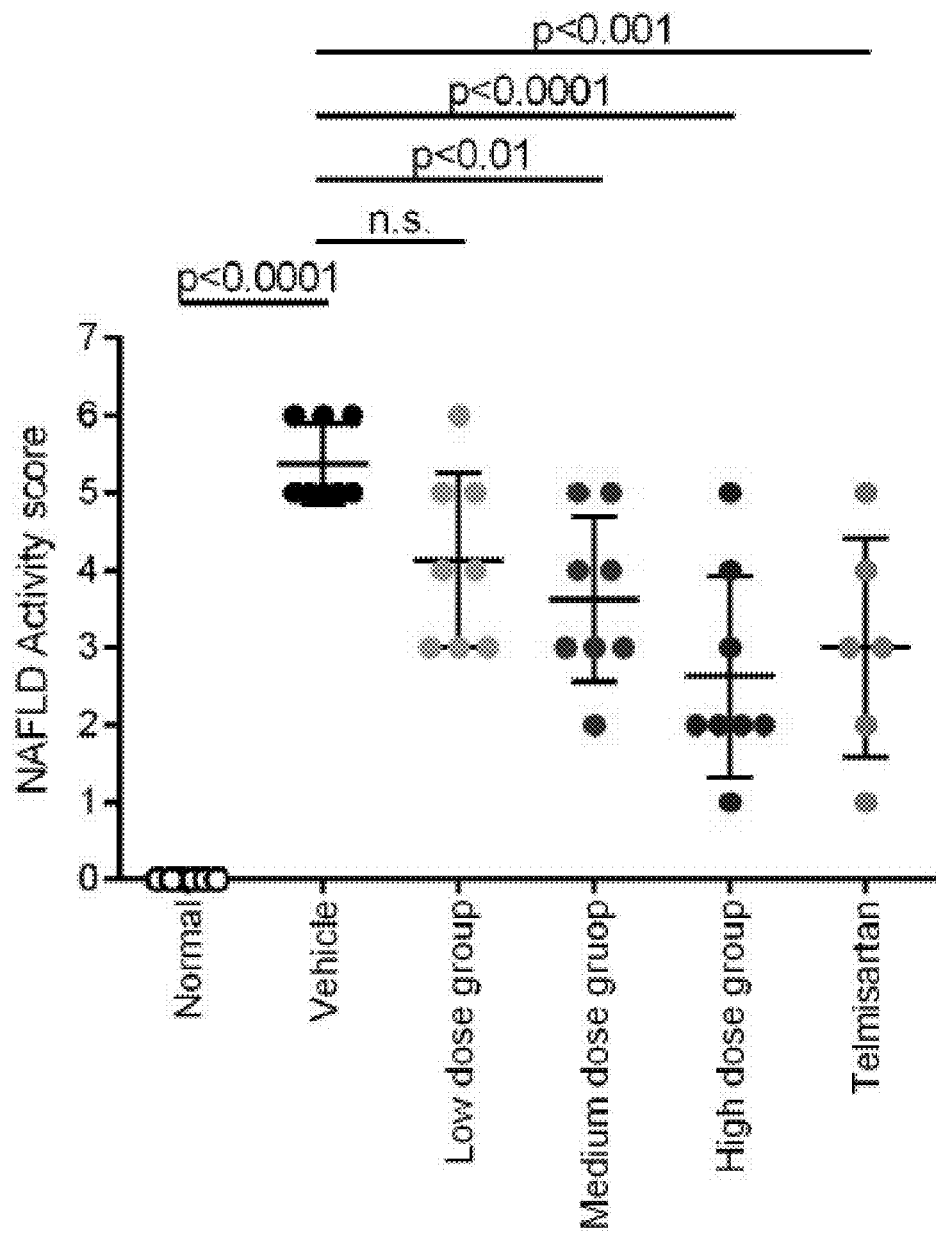
FIG. 9 is a graph showing the nonalcoholic steatohepatitis (NASH) or nonalcoholic fatty liver disease (NAFLD) activity scores calculated by aggregating the steatosis, inflammation and ballooning scores of the livers of the experimental animals in Experimental Example 9.

FIG. 9 is a graph showing the NASH or NAFLD activity scores calculated by aggregating the steatosis, inflammation and ballooning scores of the livers of the experimental animals. Referring to FIG. 9, the adenosine derivative of the inventive concept was found to have significant activity for the alleviation of NASH or NAFLD in a dose-dependent manner.

Figure 10:
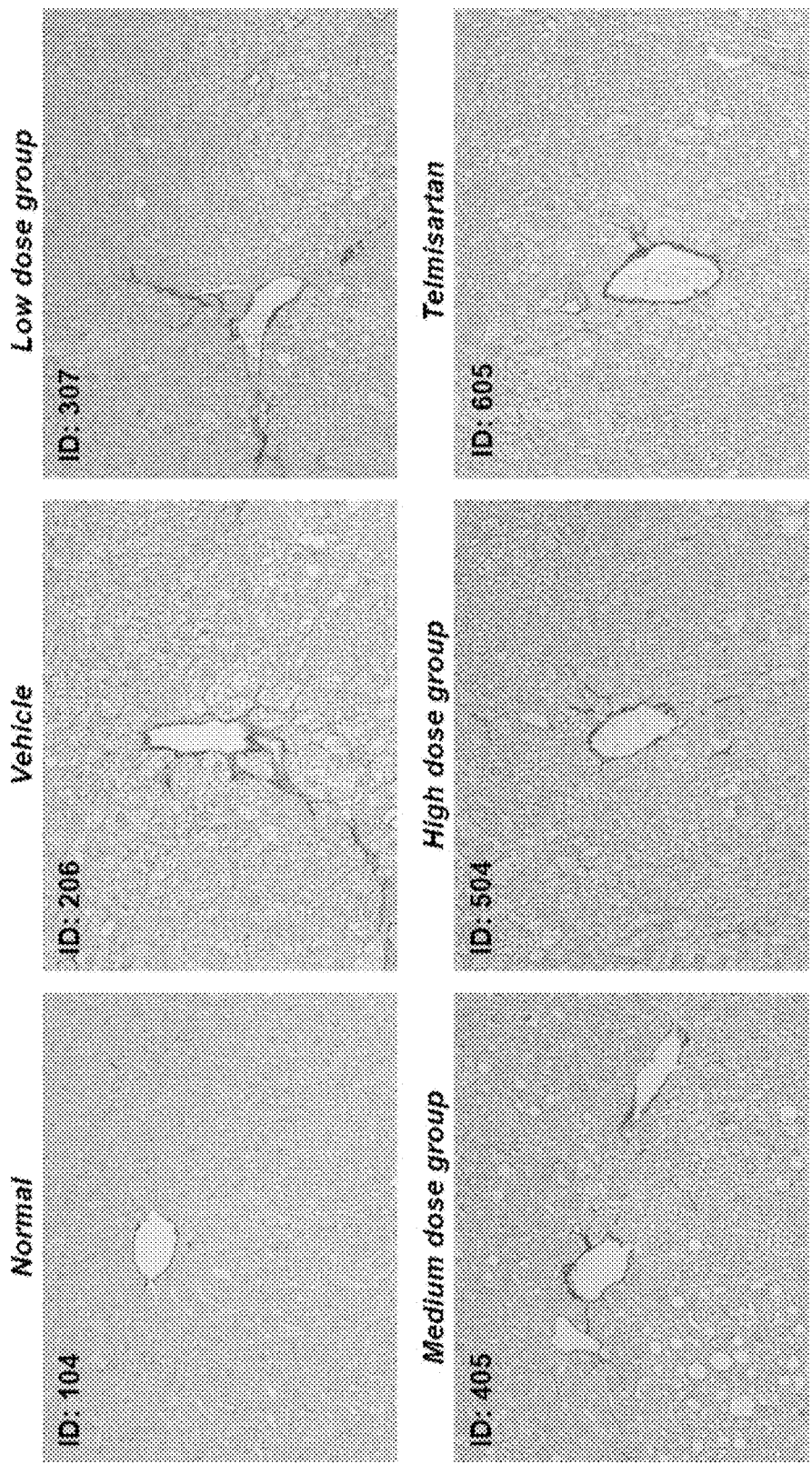
FIG. 10 is a photomicrograph showing the degrees of fibrosis of the livers of the experimental animals in Experimental Example 9.
Figure 11:
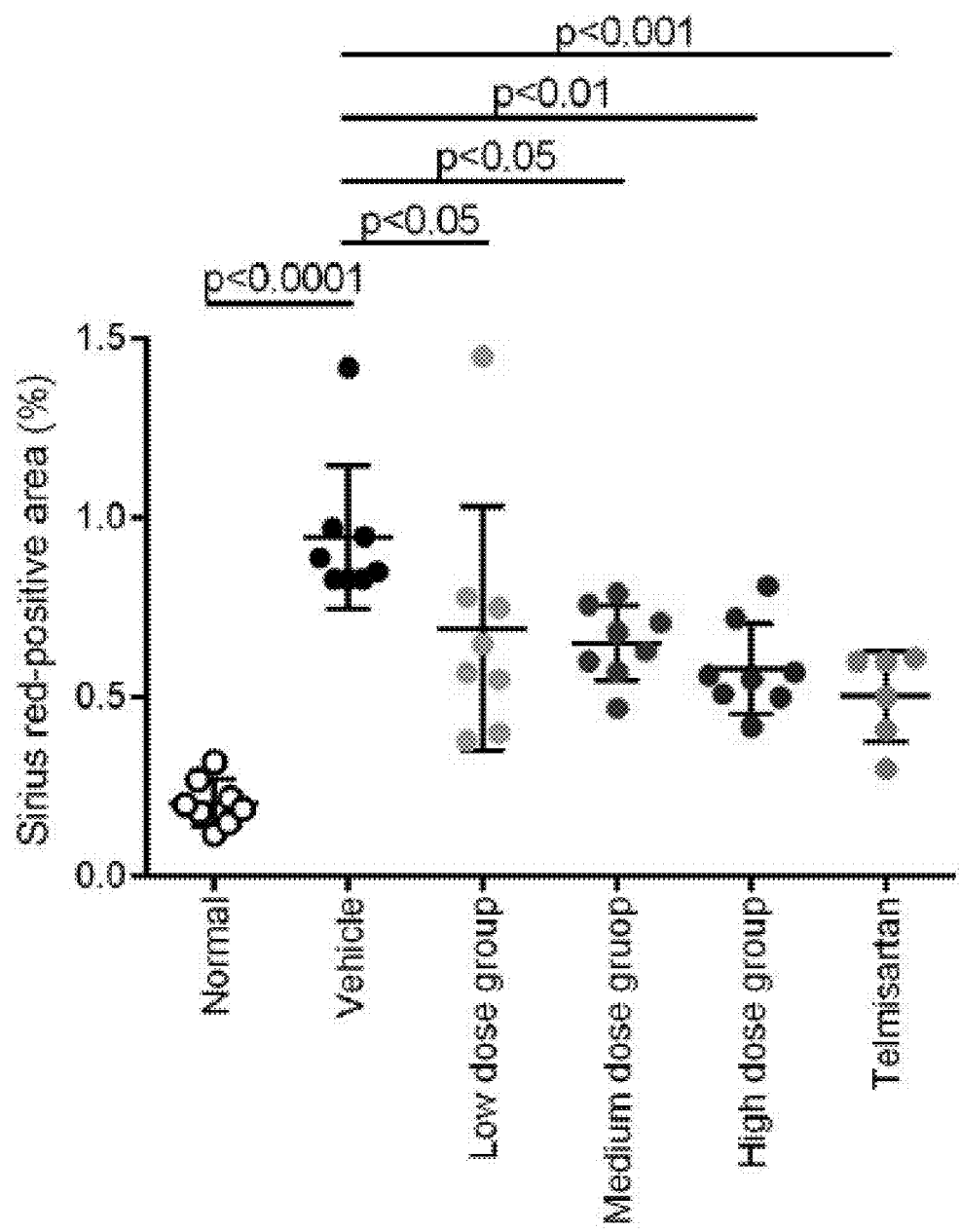
FIG. 11 is a graph showing the area of fibrosis in the livers of the experimental animals in Experimental Example 9.

FIG. 10 is a photomicrograph showing the degrees of fibrosis of the livers of the experimental animals, and FIG. 11 is a graph showing the area of fibrosis. In FIG. 10, red-stained portions are where fibrosis occurred. As is apparent from FIGS. 10 and 11, the mice administered with the adenosine derivative of the inventive concept had fibrosis-inhibitory activity dependent on the dose of the derivative, and the area of fibrosis was noticeably reduced in the mice of Experimental Example 9-1 administered with the adenosine derivative of the inventive concept at a low dose.

<Experimental Example 10> Physicochemical Properties Test of the Adenosine Derivative of the Inventive Concept In order to test the physicochemical properties of the adenosine derivative of the inventive concept, experiments were conducted on the compound of Example 2 in vitro, and the results are shown in Table 7. Plasma stability and protein binding were measured using rat and human plasma.

TABLE 7

| Physical Properties (ADME Properties) | Value |
|---|---|
| Kinetic solubility@ | 361.0 μM (148.8 μg/ml) |
| Equilibrium solubility | 6.7 μM (2.76 μg/ml) |
| Log P | 3.18 |
| pKa | 11.33 |

TABLE 7-continued

| Physical Properties (ADME Properties) | Value |
|---|---|
| PAMPA | −4.49 |
| Plasma stability | >99.9 (Rat), 98.9 (Human) |
| Plasma protein binding | 90.2(Rat), 98.7 (Human) |

As is apparent from Table 7, the adenosine derivative of the inventive concept has absorption, distribution, metabolism and excretion (ADME) properties suitable for oral administration through an oral agent.

<Experimental Example 11> Pharmacokinetic Test for Oral Administration of the Adenosine Derivative of the Inventive Concept In order to test the ADME properties of the adenosine derivative of the inventive concept after oral administration, pharmacokinetic properties of the compound of Example 2 were measured in vivo.

As shown in Table 8, the compound of Example 2 was administered to experimental animals using different administration methods. Intravenous administration was performed through a tube inserted into the femoral vein, and oral administration was performed using oral gavage.

TABLE 8

| Experimental Example | Experimental Animal | Administration Method |
|---|---|---|
| 11-1 | 8 week old SD male rat | Intravenous administration of 5 mg/kg of the compound of Example 2 |
| 11-2 | 8 week old SD male rat | Oral administration of 5 mg/kg of the compound of Example 2 |
| 12-1 | 8 week old SD male rat | Intravenous administration of 2 mg/kg of the compound of Example 2 |
| 12-2 | 8 week old SD male rat | Oral administration of 10 mg/kg of the compound of Example 2 |
| 13 | 8 week old ICR male mice | Oral administration of 10 mg/kg of the compound of Example 2 |
| 14-1 | Dog | Intravenous administration of 2 mg/kg of the compound of Example 2 |
| 14-2 | Dog | Oral administration of 10 mg/kg of the compound of Example 2 dissolved in a solvent |
| 14-3 | Dog | Oral administration of 10 mg/kg of the compound of Example 2 contained in a powder state in a capsule |
| 15-1 | 8 week old SD male rat | Oral administration of 10 mg/kg of the compound of Example 2 dissolved in 2 mL/kg of 0.5% methyl cellulose |
| 15-2 | 8 week old SD male rat | Oral administration of 10 mg/kg of the compound of Example 2 dissolved in a solvent of a mixture of 5% DMSO, 40% PEG400 and 55% DW |

After the administration, the experimental animals' blood was taken at predetermined time intervals for 24 hours. Then, the blood was centrifuged to separate plasma. The plasma samples were pretreated with a suitable organic solvent, and then the concentration of the plasma samples was analyzed by LC-MS/MS. The blood concentration-time data of the compound of Example 2 was analyzed using WinNonlin (Pharsight, USA), and graphs of the blood concentration-time data are shown in FIGS. 12 through 16. The results of noncompartmental pharmacokinetic parameters calculated from the blood concentration-time data are shown in Tables 9 through 13. In FIGS. 12 through 16, I.V. represents an intravenous administration group, P.O. represents an oral administration group, and the definition of each parameter in Tables 9 through 13 is shown in Table 14.

TABLE 9

| Parameters | I.V., 5 mg/kg | P.O., 5 mg/kg |
|---|---|---|
| $T_{max}$ (h) | NA | 1.33 ± 0.577 |
| $C_{max}$ (μg/mL) | NA | 1.45 ± 0.255 |
| $T_{1/2}$ (h) | 3.6 ± 0.589 | 3.26 ± 0.945 |
| $AUC_t$ (μg · h/mL) | 14.04 ± 2.55 | 6.98 ± 0.584 |
| $AUC_\infty$ (μg · h/mL) | 14.11 ± 2.59 | 7.04 ± 0.551 |
| CL (L/h/kg) | 0.363 ± 0.07 | NA |
| $V_{ss}$ (L/kg) | 0.881 ± 0.203 | NA |
| $F_t$ (%) | NA | 49.74 |

NA, not applicable;
ND, not detected;
NC, not calculated

TABLE 10

| Parameters | IV, 2 mg/kg | PO, 10 mg/kg |
|---|---|---|
| $T_{max}$ (hr) | — | 2.42 ± 3.13 |
| $C_{max}$ (μg/mL) | — | 2.71 ± 0.183 |
| $T_{1/2}$ (hr) | 6 ± 2.98 | 3.34 ± 0.075 |
| $AUC_t$ (μg · hr/mL) | 5.2 ± 0.548 | 26.5 ± 5.88 |
| $AUC_\infty$ (μg · hr/mL) | 5.49 ± 0.3 | 26.7 ± 0.0750 |
| CL (L/kg/hr) | 0.365 ± 0.019 | — |
| $V_{ss}$ (L/kg) | 2.27 ± 0.863 | — |
| $F_t$ (%) | — | >99.9 |

TABLE 11

| Parameters | P.O., 10 mg/kg |
|---|---|
| $T_{max}$ (h) | 6.13 ± 3.75 |
| $C_{max}$ (μg/mL) | 8.57 ± 1.52 |
| $T_{1/2}$ (h) | 3.61 ± 0.3 |
| $AUC_t$ (μg · h/mL) | 100 ± 13.2 |
| $AUC_\infty$ (μg · h/mL) | 102 ± 13.5 |
| CL (L/h/kg) | NA |
| $V_{ss}$ (L/kg) | NA |
| $F_t$ (%) | NA |

NA, not applicable;
ND, not detected;
NC, not calculated

TABLE 12

| Parameters | G1, IV, 2 mg/kg | G2, PO, 10 mg/kg | G3, PO, 10 mg/kg |
|---|---|---|---|
| $T_{max}$ (h) | NA | 1.67 ± 0.58 | 2 ± 0 |
| $C_{max}$ (μg/mL) | NA | 0.467 ± 0.073 | 1.14 ± 0.23 |
| $T_{1/2}$ (h) | 2.17 ± 0.867 | 4.21 ± 1.41 | 5.53 ± 3.06 |
| $AUC_t$ (μg · h/mL) | 0.948 ± 0.464 | 3.88 ± 1.03 | 5.64 ± 0.84 |
| $AUC_\infty$ (μg · h/mL) | 1.07 ± 0.62 | 3.99 ± 1.09 | 6.35 ± 0.83 |
| CL (L/h/kg) | 2.27 ± 1.04 | NA | NA |
| $V_{ss}$ (L/kg) | 6.02 ± 0.79 | NA | NA |
| $F_t$ (%) | NA | 82.0 | >99.9 |

NA, not applicable;
ND, not detected;
NC, not calculated

TABLE 13

| Parameters | 0.5% MC, 10 mg/kg | Vehicle, 10 mg/kg |
|---|---|---|
| $T_{max}$ (hr) | 1.33 ± 0.58 | 2.42 ± 3.13 |
| $C_{max}$ (μg/mL) | 5.72 ± 6.11 | 2.71 ± 0.183 |
| $T_{1/2}$ (hr) | 4.56 ± 2.8 | 3.34 ± 0.075 |
| $AUC_t$ (μg · hr/mL) | 40.1 ± 26.8 | 26.5 ± 5.88 |
| $AUC_\infty$ (μg · hr/mL) | 41.4 ± 26.03 | 26.7 ± 0.0750 |
| CL (L/kg/hr) | — | — |
| $V_{ss}$ (L/kg) | — | — |
| $F_t$ (%) | — | — |

TABLE 14

| Parameters | Description |
|---|---|
| $T_{max}$ (hr) | time for Cmax |
| $C_{max}$ (μg/mL) | maximum plasma concentration |
| T1/2 (hr) | terminal half-life |
| $AUC_t$ (μg · hr/mL) | areas under the plasma concentration-time curve |
| $AUC_\infty$ (μg · hr/mL) | areas under the plasma concentration-time curve from time |
| CL (L/k/hrg) | total clearance from plasma |
| $V_{ss}$ (L/kg) | steady-state volume of distribution |
| $F_t$ (%) | bioavailability ($AUC_{P.O.}/AUC_{I.V.}$) × 100 |

Figure 12:
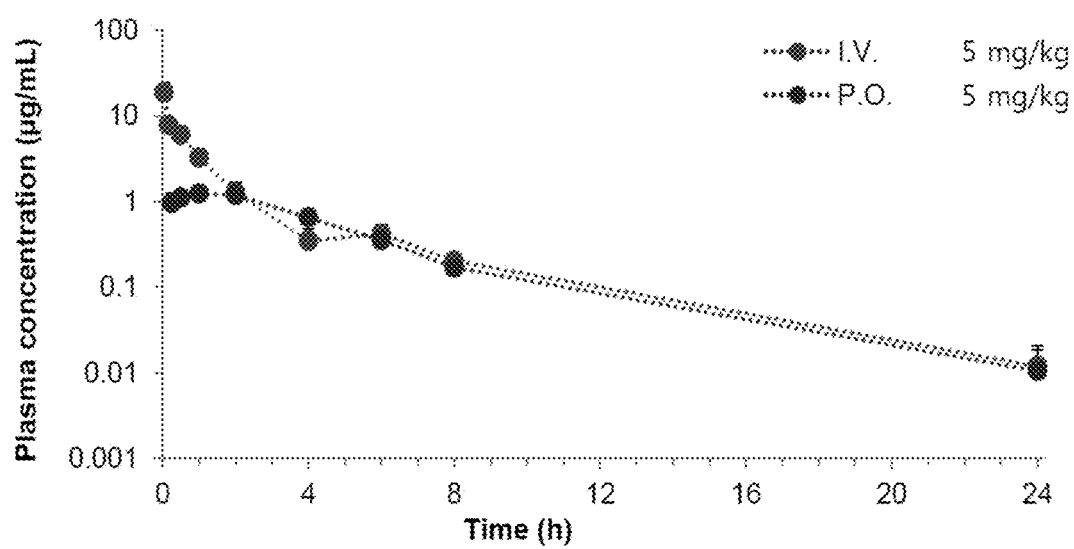
FIG. 12 is a graph obtained from the blood concentration-time data of Experimental Example 11 (11-1 and 11-2).
Figure 13:
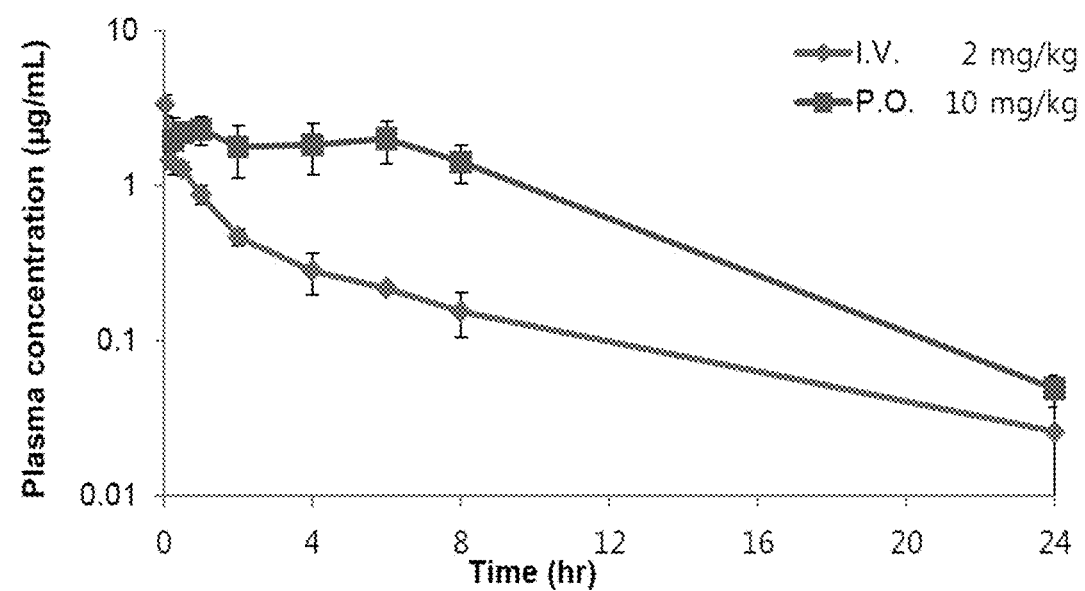
FIG. 13 is a graph obtained from the blood concentration-time data of Experimental Example 12 (12-1 and 12-2).

FIG. 12 and Table 9 show a graph and parameter values obtained from the blood concentration-time data of Experimental Example 11 (11-1 and 11-2), and FIG. 13 and Table 10 show a graph and parameter values obtained from the blood concentration-time data of Experimental Example 12 (12-1 and 12-2). Referring to FIGS. 12 and 13 and Tables 9 and 10, the adenosine derivative of the inventive concept has a long half-life $T_{1/2}$ of a maximum of 3.34 hours or more and a bioavailability $F_t$ of a maximum of 99.9% or more in the case of oral administration. Thus, the adenosine derivative of the inventive concept is more suitable for oral administration than for intravenous administration.

Figure 14:
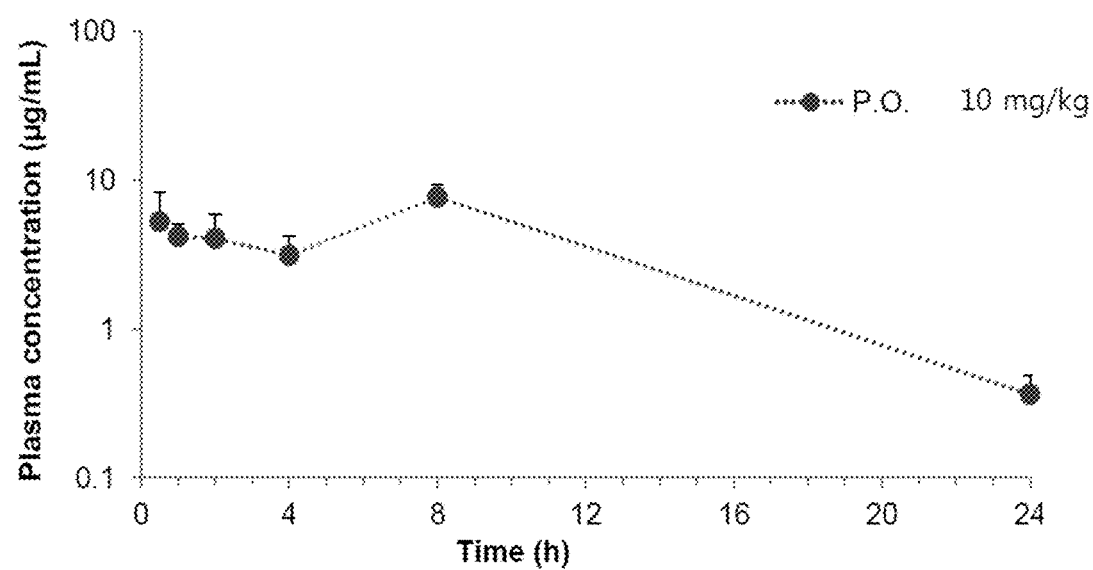
FIG. 14 is a graph obtained from the blood concentration-time data of Experimental Example 13.

FIG. 14 and Table 11 show a graph and parameter values obtained from the blood concentration-time data of Experimental Example 13. Referring to FIG. 14 and Table 11, the adenosine derivative of the inventive concept also has a long half-life $T_{1/2}$ of about 3.61 hours in mice in the case of oral administration. Thus, the adenosine derivative is suitable for oral administration.

Figure 15:
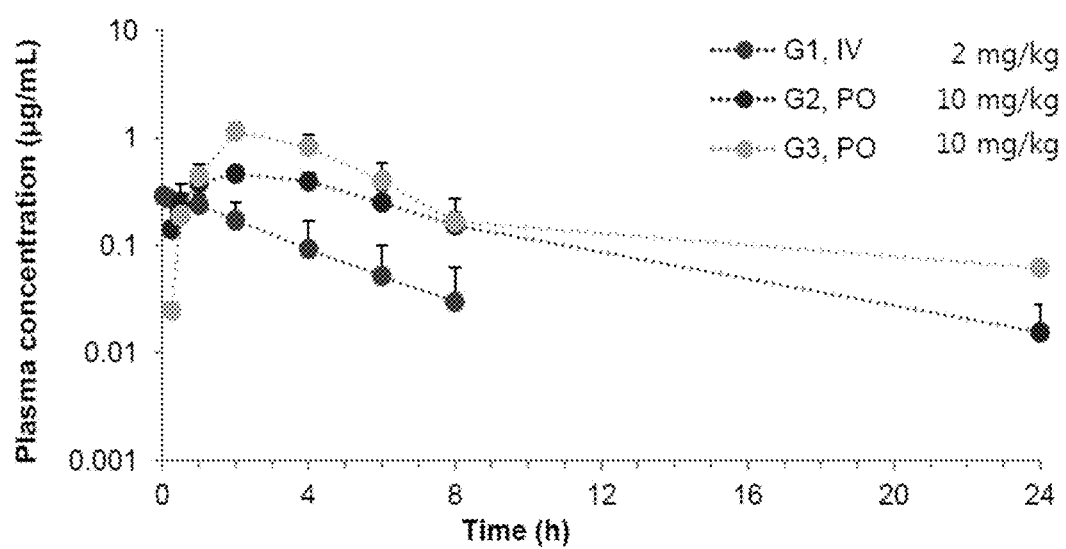
FIG. 15 is a graph obtained from the blood concentration-time data of Experimental Example 14 (14-1, 14-2 and 14-3).

FIG. 15 and Table 12 show a graph and parameter values obtained from the blood concentration-time data of Experimental Example 14 (14-1, 14-2 and 14-3). In FIG. 15, G2 and G3 respectively indicate the oral administration of the adenosine derivative of the inventive concept dissolved in a solvent and the oral administration of the adenosine derivative of the inventive concept contained in a powder state in a capsule. Referring to FIG. 15 and Table 12, the adenosine derivative of the inventive concept has a longer half-life $T_{1/2}$ of a maximum of 5.53 hours or more in dogs than in rats or mice. Thus, the adenosine derivative is suitable for oral administration. In particular, when the adenosine derivative of the inventive concept is administered in a powder state in a capsule, properties such as the half-life $T_{1/2}$ and the bioavailability $F_t$ are further improved.

Figure 16:
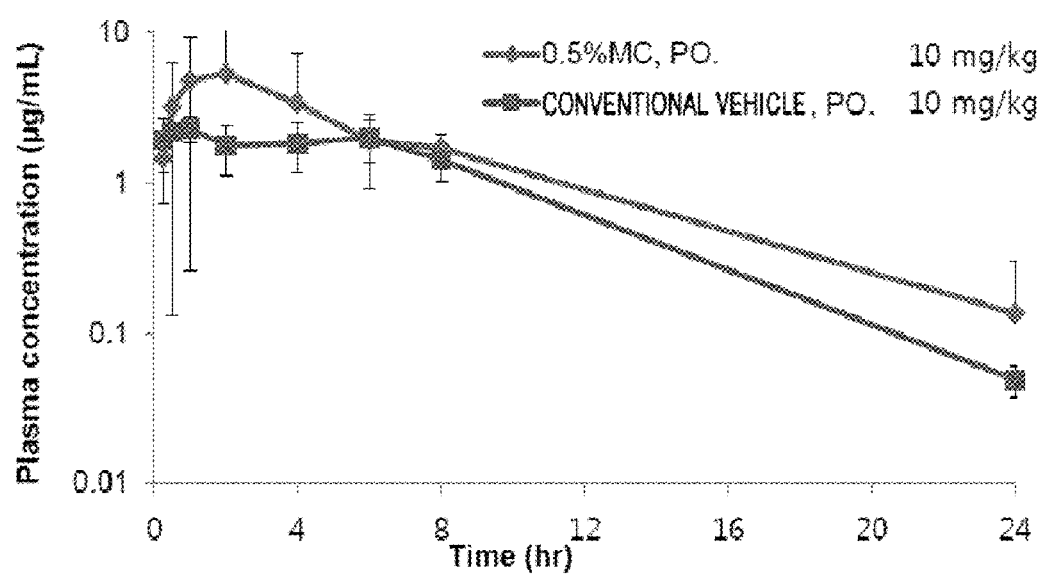
FIG. 16 is a graph obtained from the blood concentration-time data of Experimental Example 15 (15-1 and 15-2).

FIG. 16 and Table 13 show a graph and parameter values obtained from the blood concentration-time data of Experimental Example 15 (15-1 and 15-2). Referring to FIG. 16 and Table 13, the adenosine derivative of the inventive concept exhibits better properties when orally administered together with methylcellulose (MC) than when orally administered together with conventional vehicles such as dimethyl sulfoxide (DMSO), polyethylene glycol (PEG) and distilled water (DW).

<Experimental Example 16> Toxicity Test of the Adenosine Derivative of the Present Invention In order to test the toxicity of the adenosine derivative of the present invention, the compound of Example 2 was evaluated for cytotoxicity, hERG ligand binding assay, genotoxicity and single-dose toxicity.

First, a Cyto X™ cell viability assay kit was used to test the cytotoxicity of the compound of Example 2. According to the test results, the compound of Example 2 had an $IC_{50}$ of 10 μM or more in each cell line. Thus, the compound of Example 2 was evaluated as safe in terms of general cytotoxicity.

In order to test the hERG ligand binding assay of the compound of Example 2, a non-electrophysiological method was used to evaluate heart stability by evaluating fluorescence polarization according to the degree of hERG channel protein binding of a red fluorescent hERG channel ligand tracer. According to the test results, an inhibition rate for 10 μM of the compound of Example 2 was 50% or less, i.e., a standard value. Thus, the compound of Example 2 was evaluated as safe in terms of the hERG ligand binding assay.

In order to test the genotoxicity of the compound of Example 2, the gene mutagenicity of the compound of Example 2 was evaluated in the presence and absence of metabolic activation by using histidine-requiring *Salmonella* (strains TA98, TA100, TA1535 and TA1537) and tryptophan-requiring *Escherichia coli* (strain WP2uvrA (pKM101)). According to the evaluation results, the number of back-mutant colonies of the compound of Example 2 did not exceed twice the number of back-mutant colonies of the negative control group for all doses of each strain regardless of the metabolic activation, and no dose-dependent increase was observed in the compound of Example 2. In addition, for each strain, the number of back-mutant colonies in the positive control group certainly exceeded twice the number of back-mutant colonies in the negative control group. From the above results, the compound of Example 2 was evaluated as safe in terms of genotoxicity.

In order to test the single-dose toxicity of the compound of Example 2, a single dose of 2,000 mg/kg of the compound of Example 2 was administered to each of five male rats and five female rats. As a result of the test, no animals died. Thus, the compound of Example 2 was evaluated as safe in terms of single-dose toxicity.

Table 15 summarizes the above toxicity test results of the adenosine derivative of the inventive concept. As is apparent from Table 15, the adenosine derivative of the inventive concept is safe in terms of cytotoxicity, hERG ligand binding assay, genotoxicity and single-dose toxicity.

TABLE 15

| Test Type | Toxicity |
|---|---|
| Cytotoxicity evaluation | Not detected |
| hERG ligand binding assay evaluation | Not detected |
| Genotoxicity evaluation | Not detected |
| Single-dose toxicity evaluation | Not detected |

Figure 17:
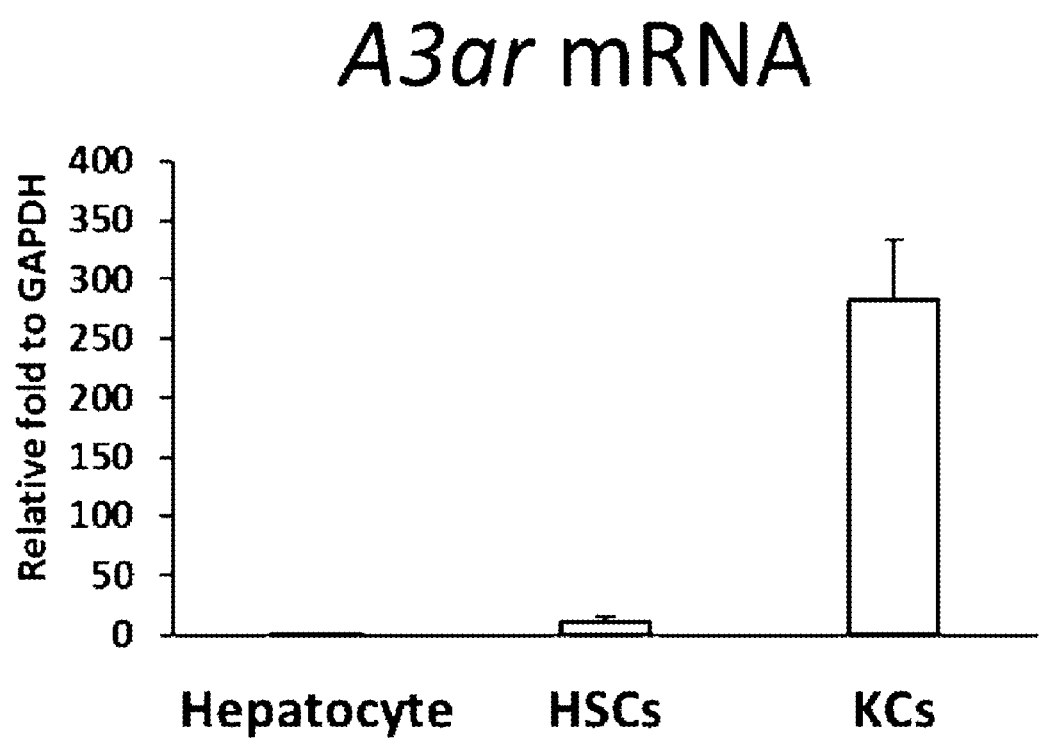
FIG. 17 is a graph showing the results of detecting the expression of an $A_3$ adenosine receptor ($A_3$ AR) through real-time polymerase chain reaction (real-time PCR) in Experimental Example 17.

<Experimental Example 17> Analysis of Expression of $A_3$ Adenosine Receptor in Major Cell Group of Liver A digestion solution (collagenase, proteinase) was directly perfused into the liver of a mouse to break down connective tissue in the liver and then to make the connective tissue into single cells. After this, hepatocytes, Kupffer cells and hepatic stellate cells were isolated. In the isolation of the hepatic stellate cells, a hepatic stellate cell-enriched fraction with specific gravity was isolated by density gradient centrifugation using Nycodenz. Finally, magnetic bead-based negative selection was conducted to isolate and culture the hepatic stellate cells. The expression of an $A_3$ adenosine receptor ($A_3$ AR) in each isolated cell group was detected by real-time PCR, and FIG. 17 is a graph showing the results. In FIG. 17, HSCs stands for hepatic stellate cells, and KCs stands for Kupffer cells.

$A_3$ AR mRNA was expressed in all of the hepatocytes, the Kupffer cells, and the hepatic stellate cells. Referring to FIG. 17, it can be seen that the expression of $A_3$ AR mRNA is particularly high in the Kupffer cells and is significant in the hepatic stellate cells.

<Experimental Example 18> Analysis of Antifibrotic Effect of Adenosine Derivative of the Inventive Concept on Hepatic Stellate Cells Hepatic stellate cells were cultured to analyze the antifibrotic effect of the compound of Example 2 on the hepatic stellate cells in an inactivated state (day 1) and in an activated state (day 3). After the hepatic stellate cells were treated with the compound of Example 2 at each concentration (2, 4 and 8 µM), the expression of Timp1, Colla1 and Acta2 (αSMA), which are representative liver fibrosis activators of the hepatic stellate cells, was analyzed by real-time PCR, and FIG. 18 is a graph showing the results.

Figure 18:
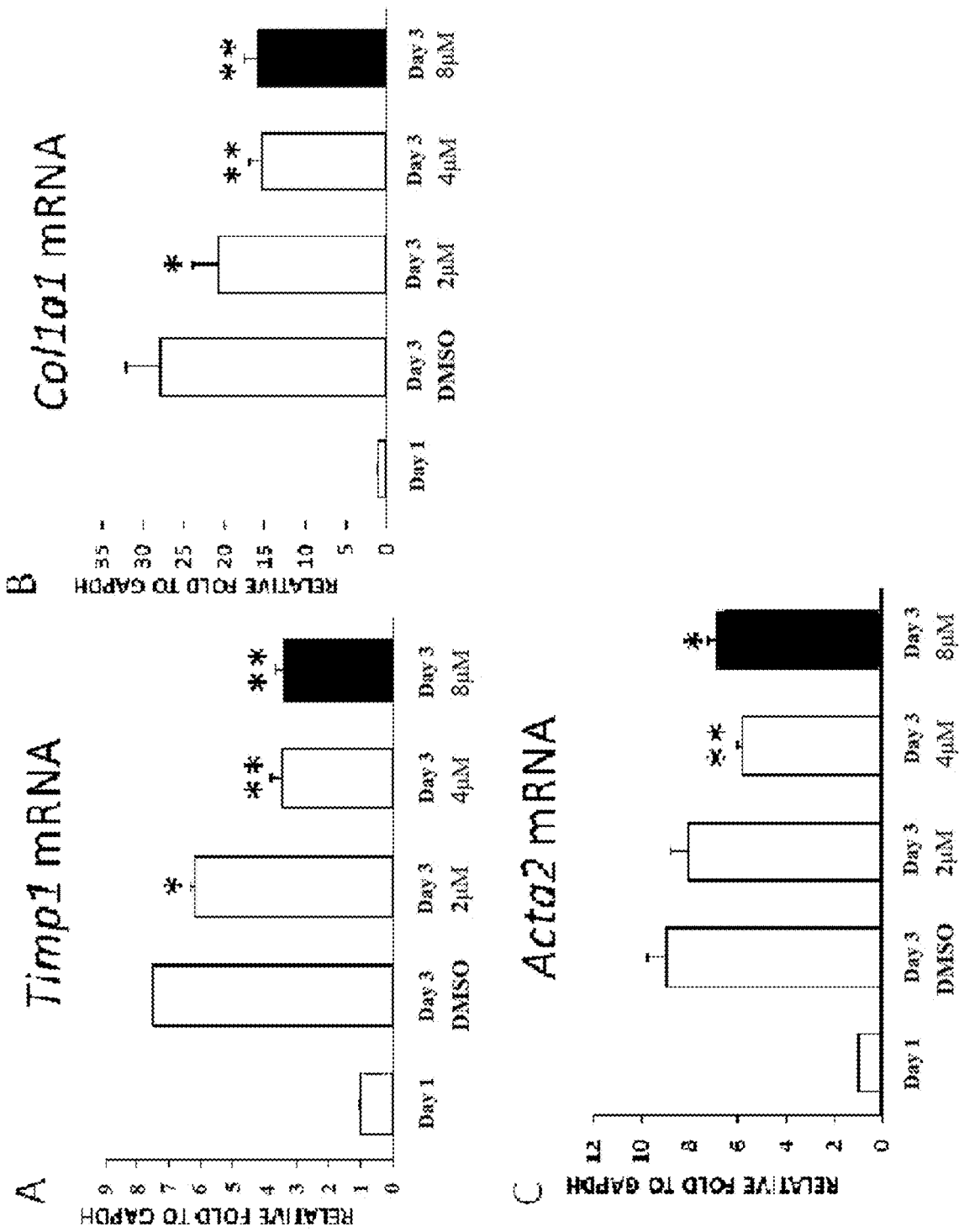
FIG. 18 is a graph showing the results of analyzing the expression of Timp1, Col1a1 and Acta2 (αSMA) through real-time PCR in Experimental Example 18.

Referring to FIG. 18, it can be seen that the expression of Timp1, which is known to induce fibrosis through inhibition of matrix metalloproteinases (MMPs), in the hepatic stellate cells is reduced in a concentration-dependent manner by the compound of Example 2 (FIG. 18A), that the expression of collagen, which is a representative extra cellular matrix (ECM) produced in activated hepatic stellate cells, is also reduced by the compound of Example 2 (FIG. 18B), and that the expression of alpha smooth muscle actin (Acta2), which is a representative marker of activated hepatic stellate cells, is also reduced in a concentration-dependent manner by the compound of Example 2 (FIG. 18C).

As apparent from FIG. 18, the antifibrotic effect of the compound of Example 2 directly affects the liver fibrosis activity of the hepatic stellate cells.

While the present invention has been particularly illustrated and described with reference to exemplary embodiments thereof, it will be understood by those of ordinary skill in the art that various changes in form and detail may be made therein without departing from the spirit and scope of the present invention as defined by the following claims. The exemplary embodiments should be considered in a descriptive sense only and not for purposes of limitation.

This research was supported by a grant of the Korea Health Technology R&D project through the Korea Health Industry Development Institute (KHIDI), funded by the Ministry of Health & Welfare, Republic of Korea (grant number: HI17C-2262-030017).

[R & D Project Supporting the Inventive Concept]
Grant number: HI17C-2262-030017
Department name: Ministry of Health and Welfare
Research management agency: Future Medicine Co., Ltd.
Research project name: Health and Medical Technology R & D Project
Title of project: Completion of Nonclinical Trials Including CMC, Toxicity and Pharmacokinetics for Clinical Phase 1 IND Approval
Contribution rate: 1/1
Host organization: Industry-Academic Cooperation Foundation of Hanyang University
Research period: 08.25, 2017-12.31, 2018

The invention claimed is:

1. A method of treating liver disease in a subject in need thereof, comprising:

providing a pharmaceutical composition comprising a compound represented by formula 1 below or a pharmaceutically acceptable salt of the compound as an active ingredient:

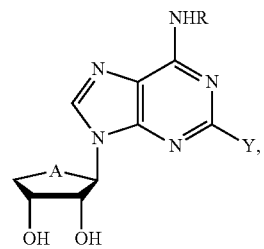

where A is S, R is a linear or branched $C_1$-$C_5$ alkyl which is non-substituted or is substituted with one or more $C_6$-$C_{10}$ aryl groups, a benzyl which is non-substituted or is substituted with halogen or one or more linear or branched $C_1$-$C_4$ alkoxy groups, or a hydroxycarbonyl-substituted benzyl, and Y is H or a halogen atom; and administering the pharmaceutical composition to the subject, wherein the liver disease is treated, wherein the liver disease comprises one or more of nonalcholic steatohepatitis (NASH) or nonalcoholic fatty liver disease (NAFLD), liver fibrosis, and liver cirrhosis.

2. The method of claim 1, wherein the formula 1 is a compound represented by formula A below:

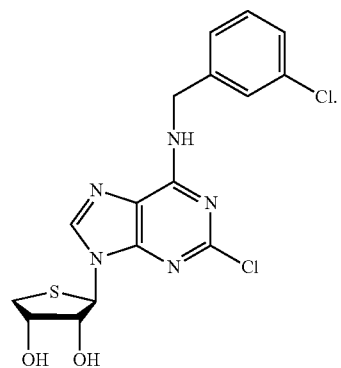

* * * * *